US011517469B2

(12) United States Patent
Hansen et al.

(10) Patent No.: US 11,517,469 B2
(45) Date of Patent: Dec. 6, 2022

(54) BASE PLATE AND SENSOR ASSEMBLY PART OF AN OSTOMY SYSTEM HAVING A MOISTURE SENSOR

(71) Applicant: Coloplast A/S, Humlebaek (DK)

(72) Inventors: Jais Ask Hansen, Jaegerspris (DK); Lars Erup Larsen, Maaloev (DK); Niels Hvid, Vedbaek (DK)

(73) Assignee: Coloplast A/S, Humlebaek (DK)

( * ) Notice: Subject to any disclaimer, the term of this patent is extended or adjusted under 35 U.S.C. 154(b) by 486 days.

(21) Appl. No.: 16/262,926

(22) Filed: Jan. 31, 2019

(65) Prior Publication Data

US 2020/0246176 A1 Aug. 6, 2020

(51) Int. Cl.
  *A61F 5/445* (2006.01)
  *A61F 5/443* (2006.01)
  *A61F 13/42* (2006.01)
  *A61B 5/00* (2006.01)

(52) U.S. Cl.
  CPC .............. *A61F 5/445* (2013.01); *A61F 5/443* (2013.01); *A61B 5/746* (2013.01); *A61F 13/42* (2013.01)

(58) Field of Classification Search
  CPC .......... A61F 5/445; A61F 5/443; A61F 13/42; A61F 13/00055; A61B 5/746
  See application file for complete search history.

(56) References Cited

U.S. PATENT DOCUMENTS

| 2,327,514 | A | 8/1943 | Fenwick |
| 2,542,233 | A | 2/1951 | Carroll |
| 2,544,579 | A | 3/1951 | Ardner |
| 4,449,970 | A | 5/1984 | Bevan et al. |
| 4,754,264 | A | 6/1988 | Okada et al. |
| 5,111,812 | A | 5/1992 | Swanson et al. |
| 5,237,995 | A | 8/1993 | Cano |
| 5,672,163 | A | 9/1997 | Ferreira et al. |
| 6,057,689 | A | 5/2000 | Saadat |

(Continued)

FOREIGN PATENT DOCUMENTS

| DE | 19953062 A1 | 5/2000 |
| DE | 102011014321 A1 | 9/2012 |

(Continued)

*Primary Examiner* — Philip R Wiest
(74) *Attorney, Agent, or Firm* — Coloplast Corp., Coloplast A/S; Nick Baumann

(57) ABSTRACT

An ostomy system configured to detect moisture content in a base plate or a sensor assembly part of the ostomy system, the ostomy system comprising the base plate and/or a sensor assembly part and a monitor device. The base plate or the sensor assembly part includes a first adhesive layer, a plurality of electrodes, and one or more sensing zones each covering one of one or more regions of the first adhesive layer, each of the one or more sensing zones including at least two of the plurality of electrodes. The monitor device is electrically coupled to the plurality of electrodes of the base plate or the sensor assembly part and configured to measure one or more resistances in the one or more sensing zones between the plurality of electrodes, each of the one or more resistances measured by two of the plurality of electrodes at one of the one or more sensing zones, and determine moisture content of the first adhesive layer at each of the one or more sensing zones based on the measured one or more resistances.

31 Claims, 17 Drawing Sheets

(56) References Cited

U.S. PATENT DOCUMENTS

| | | | |
|---|---|---|---|
| 6,135,986 A | 10/2000 | Leisner et al. | |
| 6,171,289 B1 | 1/2001 | Millot et al. | |
| 6,485,476 B1 | 11/2002 | Von Dyck et al. | |
| 6,524,675 B1 | 2/2003 | Mikami et al. | |
| 7,150,728 B2 | 12/2006 | Hansen et al. | |
| 7,166,091 B1 | 1/2007 | Zeltner | |
| 7,670,289 B1 | 3/2010 | McCall | |
| 8,398,575 B1 | 3/2013 | McCall | |
| 8,398,603 B2 | 3/2013 | Thirstrup et al. | |
| 8,795,257 B2 | 8/2014 | Coulthard et al. | |
| 8,975,465 B2 | 3/2015 | Hong et al. | |
| 9,216,104 B2 | 12/2015 | Thirstrup et al. | |
| 9,308,332 B2 | 4/2016 | Heppe | |
| 9,788,991 B2 | 10/2017 | Bird | |
| 10,016,298 B2 | 7/2018 | Thirstrup et al. | |
| D826,740 S | 8/2018 | Stevens et al. | |
| 10,799,385 B2 | 10/2020 | Hansen et al. | |
| 10,874,541 B2 * | 12/2020 | Seres | A61F 5/445 |
| 2002/0019615 A1 | 2/2002 | Roe et al. | |
| 2003/0132763 A1 | 7/2003 | Ellenz | |
| 2005/0070863 A1 | 3/2005 | Bulow et al. | |
| 2005/0085779 A1 | 4/2005 | Poulsen et al. | |
| 2005/0240163 A1 | 10/2005 | Andersen | |
| 2005/0261645 A1 | 11/2005 | Conrad et al. | |
| 2006/0025727 A1 | 2/2006 | Boehringer et al. | |
| 2006/0271002 A1 | 11/2006 | Botten | |
| 2007/0185464 A1 | 8/2007 | Fattman et al. | |
| 2008/0275327 A1 | 11/2008 | Faarbaek et al. | |
| 2008/0300559 A1 | 12/2008 | Gustafson et al. | |
| 2009/0247970 A1 | 10/2009 | Keleny et al. | |
| 2010/0010460 A1 | 1/2010 | Butler | |
| 2010/0030167 A1 * | 2/2010 | Thirslrup | A61F 13/42 604/318 |
| 2011/0034890 A1 | 2/2011 | Stroebech et al. | |
| 2012/0143154 A1 | 6/2012 | Edvardsen et al. | |
| 2012/0143155 A1 | 6/2012 | Edvardsen et al. | |
| 2012/0283678 A1 | 11/2012 | Nguyen-Demary et al. | |
| 2013/0018231 A1 | 1/2013 | Hong et al. | |
| 2013/0030167 A1 | 1/2013 | Wang et al. | |
| 2013/0030397 A1 | 1/2013 | Sabeti | |
| 2013/0072886 A1 | 3/2013 | Schertiger et al. | |
| 2013/0138065 A1 | 5/2013 | Buus | |
| 2013/0150769 A1 | 6/2013 | Heppe | |
| 2013/0192604 A1 | 8/2013 | Persson et al. | |
| 2013/0231620 A1 | 9/2013 | Thirstrup et al. | |
| 2013/0324952 A1 | 12/2013 | Krystek et al. | |
| 2014/0276501 A1 | 9/2014 | Cisko | |
| 2014/0288381 A1 | 9/2014 | Faarbaek et al. | |
| 2014/0327433 A1 | 11/2014 | Anway et al. | |
| 2015/0250639 A1 | 9/2015 | Thirstrup et al. | |
| 2015/0257923 A1 | 9/2015 | Thirstrup et al. | |
| 2016/0158056 A1 * | 6/2016 | Davis | A61F 5/443 604/318 |
| 2016/0166438 A1 | 6/2016 | Rovaniemi | |
| 2016/0235581 A1 | 8/2016 | Keleny et al. | |
| 2016/0310140 A1 * | 10/2016 | Belson | A61B 5/14532 |
| 2017/0055896 A1 * | 3/2017 | Al-Ali | A61B 5/113 |
| 2017/0140103 A1 | 5/2017 | Angelides | |
| 2017/0340474 A1 * | 11/2017 | Thirstrup | A61F 5/443 |
| 2018/0049667 A1 * | 2/2018 | Heppe | A61M 1/3656 |
| 2018/0055359 A1 * | 3/2018 | Shamim | A61B 5/14539 |
| 2018/0171183 A1 | 6/2018 | Sakurai et al. | |
| 2019/0133810 A1 * | 5/2019 | Seres | A61F 5/441 |
| 2019/0133812 A1 | 5/2019 | Seres et al. | |
| 2019/0175386 A1 | 6/2019 | Monty | |
| 2019/0192332 A1 | 6/2019 | Hansen et al. | |
| 2019/0192333 A1 | 6/2019 | Hansen et al. | |
| 2019/0192334 A1 | 6/2019 | Hansen et al. | |
| 2019/0247050 A1 | 8/2019 | Goldsmith | |
| 2020/0188161 A1 | 6/2020 | Seres et al. | |
| 2020/0246174 A1 | 8/2020 | Hansen et al. | |
| 2020/0246175 A1 | 8/2020 | Hansen et al. | |
| 2020/0246176 A1 | 8/2020 | Hansen et al. | |
| 2020/0246177 A1 | 8/2020 | Hansen et al. | |
| 2020/0276063 A1 * | 9/2020 | Munoz | A61F 13/58 |
| 2020/0306074 A1 | 10/2020 | Speiermann et al. | |
| 2020/0330258 A1 | 10/2020 | Hansen et al. | |
| 2020/0330260 A1 | 10/2020 | Hansen et al. | |
| 2020/0337880 A1 | 10/2020 | Hansen et al. | |
| 2020/0337881 A1 | 10/2020 | Hansen et al. | |
| 2020/0337883 A1 | 10/2020 | Hansen et al. | |
| 2020/0375784 A1 | 12/2020 | Hansen et al. | |
| 2020/0375785 A1 | 12/2020 | Hansen et al. | |
| 2020/0375786 A1 | 12/2020 | Hansen et al. | |
| 2020/0383637 A1 | 12/2020 | Hansen et al. | |
| 2020/0383818 A1 | 12/2020 | Hansen et al. | |
| 2020/0383819 A1 | 12/2020 | Sletten et al. | |
| 2020/0383820 A1 | 12/2020 | Hansen et al. | |
| 2020/0383821 A1 | 12/2020 | Hansen et al. | |
| 2020/0390587 A1 | 12/2020 | Svanegaard et al. | |
| 2020/0390588 A1 | 12/2020 | Hansen et al. | |
| 2020/0390589 A1 | 12/2020 | Hansen et al. | |
| 2020/0395120 A1 | 12/2020 | Svanegaard et al. | |
| 2020/0405228 A1 | 12/2020 | Svanegaard et al. | |
| 2020/0405229 A1 | 12/2020 | Svanegaard et al. | |
| 2020/0405230 A1 | 12/2020 | Svanegaard et al. | |
| 2021/0000414 A1 | 1/2021 | Svanegaard et al. | |
| 2021/0000633 A1 | 1/2021 | Hansen et al. | |
| 2021/0000634 A1 | 1/2021 | Svanegaard et al. | |
| 2021/0007663 A1 | 1/2021 | Svanegaard et al. | |
| 2021/0007881 A1 | 1/2021 | Svanegaard et al. | |
| 2021/0015654 A1 | 1/2021 | Hansen et al. | |
| 2021/0038424 A1 | 2/2021 | Svanegaard et al. | |
| 2021/0059603 A1 | 3/2021 | Svanegaard et al. | |
| 2021/0085511 A1 | 3/2021 | Hansen et al. | |
| 2021/0085512 A1 | 3/2021 | Hansen et al. | |
| 2021/0177642 A1 | 6/2021 | Andersen et al. | |
| 2021/0212855 A1 | 7/2021 | Hansen et al. | |
| 2021/0338471 A1 | 11/2021 | Nolan et al. | |
| 2021/0361464 A1 | 11/2021 | Larsen et al. | |
| 2021/0361465 A1 | 11/2021 | Hansen et al. | |
| 2021/0361467 A1 | 11/2021 | Hansen et al. | |
| 2021/0369197 A1 | 12/2021 | Hansen et al. | |
| 2021/0369488 A1 | 12/2021 | Hansen et al. | |
| 2021/0369489 A1 | 12/2021 | Hansen et al. | |
| 2021/0369490 A1 | 12/2021 | Hansen et al. | |

FOREIGN PATENT DOCUMENTS

| | | |
|---|---|---|
| DE | 102011076219 A1 | 11/2012 |
| EP | 0896211 A2 | 2/1999 |
| GB | 2343628 A | 5/2000 |
| GB | 2542093 A | 3/2017 |
| JP | H11128352 A | 5/1999 |
| JP | 2002055074 A | 2/2002 |
| JP | 2005323981 A | 11/2005 |
| KR | 20120003987 A | 1/2012 |
| TW | 201201783 A | 1/2012 |
| WO | 9933037 A1 | 7/1999 |
| WO | 0079497 A1 | 12/2000 |
| WO | 2006008866 A1 | 1/2006 |
| WO | 2007098762 A1 | 9/2007 |
| WO | 2015014774 A1 | 2/2015 |
| WO | 2017067558 A1 | 4/2017 |
| WO | 2017088153 A1 | 6/2017 |
| WO | 2019094635 A1 | 5/2019 |

* cited by examiner

BASE PLATE AND SENSOR ASSEMBLY PART OF AN OSTOMY SYSTEM HAVING A MOISTURE SENSOR

The present disclosure relates to an ostomy system, devices thereof and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
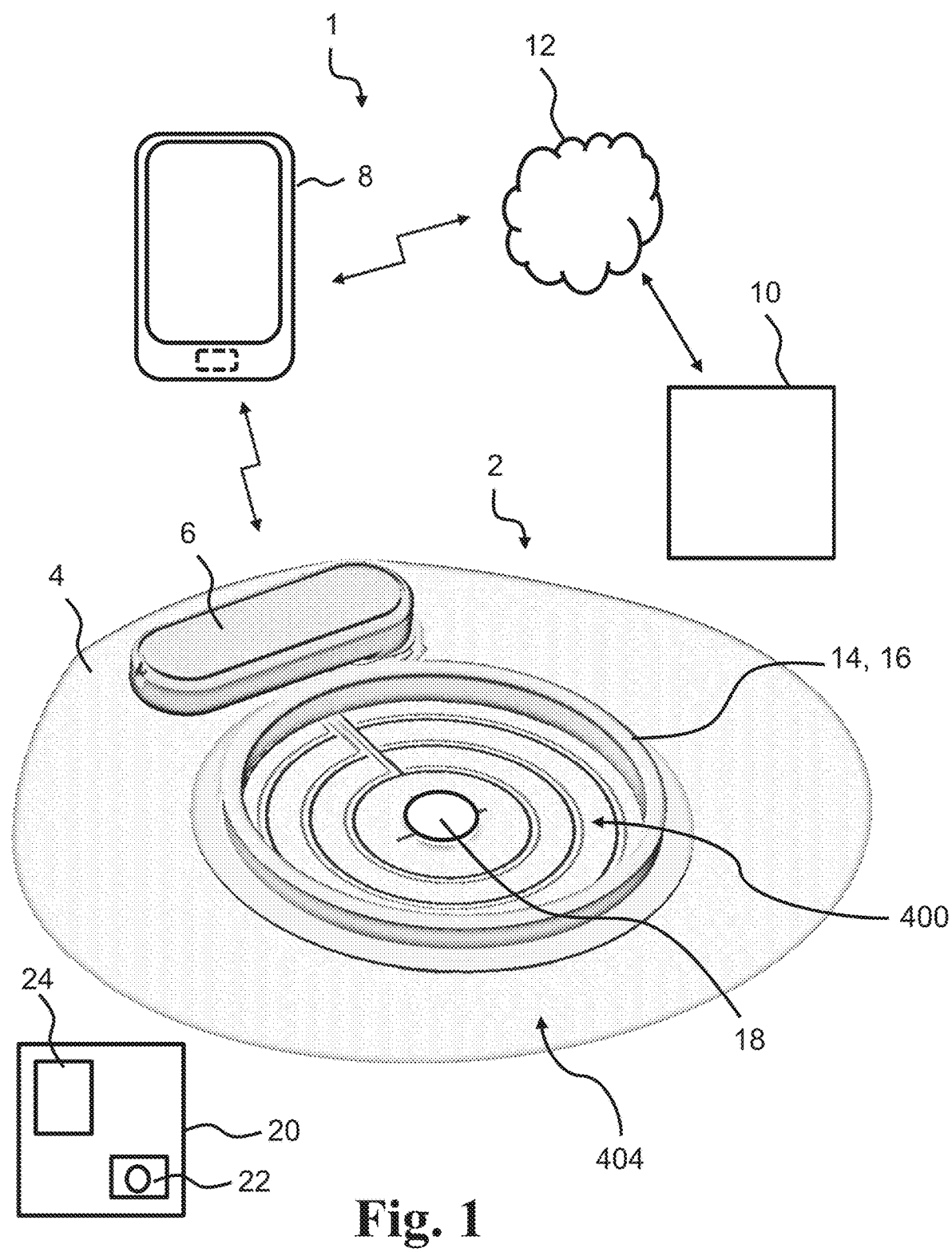
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocoloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition.

The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocoloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage, or an imminent leakage. The sensing part may be suitable for sensing e.g. by its shape, said shape potentially being circular, oval, or rectangular. Thus, the conductor part may conduct a signal arising from the sensing part. An electrode may comprise alternating conductor parts and sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or of the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part may comprise a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or of the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or of the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or of the sensor assembly part, such as of the electrode assembly. The first intermediate element may be arranged between the terminal elements and the first adhesive layer. The first intermediate element may cover or overlap terminal element(s) of the base plate and/or of the sensor assembly part when seen in the axial direction. Thus, the first adhesive layer may be protected or experience more evenly distributed mechanical stress from the terminal elements of the base plate and/or of the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or of the sensor assembly part.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening with a center point, alternatively such opening may be denoted a central opening. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determining an operating state of the base plate and/or the sensor assembly part of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate and/or the sensor assembly part via the second interface; and/or in accordance with a determination that the operating state is a second operating state, transmit a second monitor signal comprising monitor data indicative of the second operating state of the base plate and/or the sensor assembly part via the second interface.

In one or more exemplary monitor devices, the first operating state of the base plate and/or of the sensor assembly part corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate and/or the sensor assembly part corresponds to a situation wherein the first adhesive layer of the base plate and/or of the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate and/or the sensor assembly part is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate and/or the sensor assembly part may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by (P_1_1<TH_1_1), (P_2_1>TH_1_2), and (P_3_1>TH_1_3), wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value, and wherein the first operating state is indicative of low degree of radial erosion on the base plate and/or the sensor assembly part. The first threshold values (TH_1_1, TH_1_2 and TH_1_3) may be the same or different, e.g. depending on the electrode configuration of the base plate and/or the sensor assembly part. The first tertiary criterion (P_3_1<TH_1_3) may be omitted in the first criteria set.

The first primary parameter P_1_1 may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate and/or the sensor assembly part is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate and/or the sensor assembly part is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by (P_1_1<TH_2_1), (P_2_1<TH_2_2), and (P_3_1>TH_2_3)

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate and/or the sensor assembly part.

The second threshold values (TH_2_1, TH_2_2 and TH_2_3) may be the same or different, e.g. depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate and/or the sensor assembly part is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by (P_1_1>TH_D_1), (P_2_1>TH_D_2), and (P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or of the sensor assembly part.

In one or more exemplary monitor devices, to determine an operating state of the base plate and/or the sensor assembly part is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate and/or of the sensor assembly part corresponds to a situation wherein the first adhesive layer of the base plate and/or of the sensor assembly part has experienced a third degree of radial erosion, e.g. the first adhesive layer is eroded to the third radial distance of the third electrode pair.

The third criteria set may be given by (P_1_1<TH_3_1), (P_2_1<TH_3_2), and (P_3_1>TH_3_3)

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or of the sensor assembly part. The third threshold values (TH_3_1, TH_3_2 and TH_3_3) may be the same or different, e.g. depending on the electrode configuration of the base plate and/or the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair (first leakage electrode and second leakage electrode) of the base plate and/or of the sensor assembly part. To apply a processing scheme may comprise to obtain fourth parameter data based on the fourth ostomy data, and determine an operating state of the base plate and/or the sensor assembly part of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate and/or the sensor assembly part corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by (P_4_1<TH_4_4)

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped. Additionally or alternatively, the monitor device may be rigid or flexible.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery. Additionally or alternatively, the sensor terminal may change its function if the charging voltage is sensed at relevant terminals.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, and Bluetooth 5. The second interface optionally comprises a loudspeaker and/or a haptic feedback element for provision of an audio signal and/or haptic feedback to the user, respectively.

The monitor device may be electrically coupled to the plurality of electrodes of the base plate and/or the sensor assembly part. For example, the monitor device may be couplable, such as releasably couplable, to the plurality of electrodes of the base plate and/or the sensor assembly part. The monitor device may be configured to measure one or more resistances between the plurality of electrodes, and detect the leakage of output based on the measured one or more resistances.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is an ostomy system, such as an ostomy system as disclosed above. The ostomy system may be configured to detect and/or estimate moisture content in a base plate and/or a sensor assembly part of the ostomy system, such as in an adhesive layer of the base plate and/or sensor assembly part, such as in a first adhesive layer of the base plate and/or sensor assembly part.

Also disclosed is a base plate, a sensor assembly part and a monitor device. The ostomy system may comprise the base plate, and/or the sensor assembly part, and/or the monitor device.

The base plate and/or the sensor assembly part includes a first adhesive layer having a distal surface and a proximal surface. The proximal surface may be configured for attachment of the base plate and/or sensor assembly part to the skin surface of a user. The first adhesive layer may have a stomal opening with a center point. The base plate and/or the sensor assembly part further includes a plurality of electrodes disposed on the distal surface of the first adhesive layer, e.g. the plurality of electrodes may be provided as an electrode assembly as described above being positioned on the distal surface of the first adhesive layer. The base plate and/or the sensor assembly part further includes one or more sensing zones, e.g. including a first sensing zone, a second sensing zone and/or a third sensing zone. Each sensing zone covering one of one or more regions of the first adhesive layer. Any of the one or more sensing zones may cover a region of the first adhesive layer different from any other region of the first adhesive layer covered by another of the one or more sensing zones. For example, the first sensing zone may cover a region of the first adhesive layer different from a region of the first adhesive layer covered by the second sensing zone and/or different from a region of the first adhesive layer covered by the third sensing zone. Each sensing zone may include at least two of the plurality of electrodes. For example, the first sensing zone may include a first electrode and a ground electrode of the plurality of electrodes, the second sensing zone may include a second electrode and the ground electrode of the plurality of electrodes, and/or the third sensing zone may include a third electrode and the ground electrode of the plurality of electrodes. The covered regions of the one or more sensing zones may overlap but not in totality.

The monitor device may be electrically couplable to the plurality of electrodes of the base plate and/or the sensor assembly part, e.g. the monitor device may be electrically coupled to the plurality of electrodes of the base plate and/or the sensor assembly part.

The monitor device is configured to measure resistances between pair of electrodes, as described in more detail above. For example, the monitor device is configured to measure one or more resistances in the one or more sensing zones via the plurality of electrodes. Each of the one or more resistances is measured between two of the plurality of electrodes at one of the one or more sensing zones. For example, the monitor device may be configured to measure a first resistance in the first sensing zones between the first electrode and the ground electrode, the monitor device may be configured to measure a second resistance in the second sensing zones between the second electrode and the ground electrode, and/or the monitor device may be configured to measure a third resistance in the third sensing zones between the third electrode and the ground electrode.

The monitor device may further be configured to determine and/or estimate moisture content, e.g. a relative moisture content with respect to a base line, of the first adhesive layer at each of the one or more sensing zones based on the measured one or more resistances. Determining and/or estimating moisture content may be determining a change, such as an increase and/or decrease, in moisture content. For example, the monitor device may be configured to determine moisture content of the first adhesive layer at the first sensing zones based on the measured first resistance, the monitor device may be configured to determine moisture content of the first adhesive layer at the second sensing zones based on the measured second resistance, and/or the monitor device may be configured to determine moisture content of the first adhesive layer at the third sensing zones based on the measured third resistance. Alternatively or additionally, the monitor device may be configured to determine and/or estimate base plate status, such as remaining wear time, leakage risk, adhesive performance of the first adhesive layer, risk of detachment of the first adhesive layer, etc. based on the measured one or more resistances.

A sensing zone, such as any of the one or more sensing zones, such as the first sensing zone and/or the second sensing zone may be defined by two electrodes of the plurality of electrodes. For example, a sensing zone, such as any of the one or more sensing zones, such as the first sensing zone and/or the second sensing zone may be a region of the first adhesive layer between the two electrodes of the plurality of electrodes. For example, the first sensing zone may be a region of the first adhesive layer between the first electrode and the ground electrode, and/or the second sensing zone may be a region of the first adhesive layer between the second electrode and the ground electrode, and/or the third sensing zone may be a region of the first adhesive layer between the third electrode and the ground electrode.

The one or more sensing zones may be arranged circularly, such as angularly, about, radially from, and/or concentrically about a stomal opening of the base plate and/or the sensor assembly part. For example, the one or more sensing zones may be arranged angularly about the stomal opening of the base plate and/or the sensor assembly part. Alternatively or additionally, the one or more sensing zones may be arranged radially from the stomal opening of the base plate and/or the sensor assembly part. Alternatively or additionally, the one or more sensing zones may be arranged concentrically about the stomal opening of the base plate and/or the sensor assembly part.

The one or more sensing zones, such as a plurality of the one or more sensing zones, may be spaced radially and/or angularly with respect to a center point of the stomal opening.

For example, the first sensing zone may be arranged in a first angle space from the center point, the second sensing zone may be arranged in a second angle space from the center point, and/or the third sensing zone may be arranged in a third angle space from the center point. The first angle space may span a first angle in the range from 45° to 315°, such as in the range from 45° to 135°. The second angle space may span a second angle in the range from 45° to 315°, such as in the range from 45° to 135°. The third angle space may span a third angle in the range from 45° to 315°, such as in the range from 45° to 135°. The first, second, and/or third angle may depend on the number of angular sensing zones on the base plate and/or the sensor assembly part. For example, the first, second and/or third angle may be about 180°±15°, e.g. for a base plate and/or a sensor assembly part with two or more angular sensing zones. The first, second and/or third angle may be about 120°±15°, e.g. for a base plate and/or a sensor assembly part with two, three or more sensing zones. The first, second and/or third angle may be about 90°±15°, e.g. for a base plate and/or a sensor assembly part with two, three, four or more sensing zones.

Alternatively or additionally, the first sensing zone may be arranged in a first radial space from the center point, the second sensing zone may be arranged in a second radial space from the center point, and/or the third sensing zone may be arranged in a third radial space from the center point. The first radial space may span a primary radius in the range from 5-40 mm, such as in the range from 10-25 mm, such as in the range from 13-14 mm. The second radial space may span a second radius in the range from 10-50 mm, such as in the range from 10-25 mm, such as in the range from 19-20 mm. The third radial space may span a third radius in the range from 15-50 mm, such as in the range from 20-30 mm, such as in the range from 25-26 mm. The first, second and/or third radius may depend on the number of radial sensing zones on the base plate and/or the sensor assembly part. The second radius may be greater than the first radius. The third radius may be greater than the second radius and/or the first radius.

The monitor device may be configured to detect and/or estimate a moisture pattern in the first adhesive layer based on the measured one or more resistances. For example, the moisture pattern may include regions of the first adhesive layer covered by and/or between the sensing zones where resistances have measured to be indicative of elevated moisture contents. Because changes in water content changes conductivity of the first adhesive layer, the monitor device may derive a moisture content, e.g. a relative moisture content with respect to a baseline, based on the measured one or more resistances.

The plurality of electrodes, such as portions of the plurality of electrodes, such as sensing parts of the plurality of electrodes, may be distributed on concentric circles about the stomal opening of the base plate and/or the sensor assembly part. The plurality of electrodes, such as portions of the plurality of electrodes, such as sensing parts of the plurality of electrodes, may extend at least three-quarters of the circumferences of the corresponding concentric circles. For example, portions, such as sensing parts, of the plurality of electrodes may extend about the stomal opening and/or extend at least three-quarters of the circumferences about the stomal opening. Alternatively or additionally, the plurality of electrodes, such as portions of the plurality of electrodes, such as sensing parts of the plurality of electrodes, may extend less than full circles to form open loops. For example, portions, such as sensing parts, of the plurality of electrodes may extend about the stomal opening and extend less than full circles to form open loops.

The monitor device may be configured to detect an elevated moisture content, e.g. by measuring one or more resistances below a predetermined threshold, such as a resistance threshold. The monitor device may be configured to generate a wetted signal.

The monitor device may be configured to generate the wetted signal when the moisture content in the first adhesive layer, e.g. at any of the one or more sensing zones is determined to be elevated, such as above a predetermined threshold. The monitor device may be configured to generate the wetted signal when the measured one or more resistances indicates that the moisture content is elevated. For example, the monitor device may be configured to generate the wetted signal when the measured one or more resistances is below a predetermined threshold, such as a resistance threshold.

The wetted signal may be indicative of a wetted region, e.g. the wetted region may include sensing zones where the measured resistances have dropped below the resistance threshold.

The monitor device may be configured to detect whether an elevated moisture content is elevated in a plurality of the one or more sensing zones. The monitor device may be configured to generate a collectively-wetted signal. The monitor device may be configured to generate a collectively-wetted signal when the moisture content in the first adhesive layer in a plurality of the one or more sensing zones, such as the first sensing zone and the second sensing zone and optionally the third sensing zone, are substantially the same and determined to be elevated, such as above a predetermined threshold. The monitor device may be configured to generate the collectively-wetted signal when a plurality of the measured one or more resistances indicates substantially the same moisture content and determines the moisture content to be elevated. For example, the monitor device may be configured to generate the collectively-wetted signal when the plurality of the measured one or more resistances are below a predetermined threshold, such as a resistance threshold.

The collectively-wetted signal may be indicative of a wetted region, e.g. the wetted region may include sensing zones where the measured resistances have dropped below the resistance threshold.

The monitor device may be configured to determine rate of change of each of the one or more resistances measured in the one or more sensing zones. For example, the monitor device may be configured to determine a first rate of change of the first resistance measured in the first sensing zone, the monitor device may be configured to determine a second rate of change of the second resistance measured in the second sensing zone, and/or the monitor device may be configured to determine a third rate of change of the third resistance measured in the third sensing zone. Further, the monitor device may be configured to determine a wetted type based on the determined rate of change, such as the first, second and/or third rate of change. The wetted type may be indicative of a presumed cause of the change of resistance in the one or more sensing zone, such as the first, second and/or third sensing zone. The monitor device may be configured to determine that the wetted type is indicative of output causing the change of resistance in the one or more sensing zone if the determined rate of change is above a first rate threshold. The monitor device may be configured to determine that the wetted type is indicative of sweat causing the change of resistance in the one or more sensing zone if the determined rate of change is below a second rate threshold. The first rate threshold may be the same as the second rate threshold. Alternatively, the first rate threshold may be greater than the second rate threshold.

It may be useful to introduce an instant relative decay (IRD) in order to differentiate leakage from moisture absorption. The IRD is equal to the difference (typically a fall in resistance, i.e. a decay) between a measured data point (e.g. a numerical value of the resistance across a sensor) and the previously measured data point (e.g. another numerical value of the resistance across a sensor), divided by the maximum possible difference (decay). The maximum decay may be the situation going from a baseline measurement of a healthy base plate and/or sensor assembly part, to a situation where the resistance has fallen to zero, i.e. indicative of a short-circuited sensor. Thus, the instant relative decay (IRD) is given by;

$$IRD = \frac{|A_2 - A_1|}{A_{max}} \times 100\%$$

where A2 and A1 are the previously measured data point (at time $t_2$) and the present data point (at time $t_1$), respectively, and where Amax is the largest possible decay. For resistance measurements, Amax may be the absolute value of the resistance across a sensor in a healthy base plate and/or sensor assembly part. The difference $A_2-A_1$ may be denominated an actual decay, as it relates to the decay in the measured parameter at present relative to the previously measured value of the parameter. Preferably, the modulus (absolute value) of the actual decay is considered.

The monitor device and/or the accessory device may be configured to determine an instant relative decay based on the measured resistance measured across the one or more sensors and/or in the one or more sensing zones. Therefrom, the monitor device and/or the accessory device may be configured to determine the condition of the base plate/and or the sensor assembly part.

It should be noted that other parameters than resistance may be monitored, as described previously. Further, it should be noted that the formula does not require a certain unit (for resistance measurements; ohm), as only a relative change is considered. As such, a signal proportional to the resistance across the sensor is sufficient to calculate the IRD.

The data point sampling rate may be from 1 Hz (every second) to 0.017 Hz (every 60th second), or even higher or lower, depending on the settings of the monitor device and/or the accessory device. A higher sampling rate results in a higher power usage. Thus, the difference $t_2-t_1$ may correspond the interval between consecutively measured data points according to the given data point sampling rate. The data point sampling rate may be adaptive to the condition of the base plate and/or the sensor assembly plate. For example, the sampling rate may be increased if a tendency of increasing IDS is observed. Thereby, power is saved when the base plate and/or the sensor assembly part is considered healthy, and may instead be directed to the situation where the base plate and/or the sensor assembly part is deteriorating.

The monitor device and/or the accessory device may determine/calculate the IRD based on the measured raw data. Alternatively, the monitor device and/or the accessory device may determine/calculate a moving average based on the measured raw data prior to determining/calculating the IRD. Thus, the monitor device/and or the accessory device may determine/calculate the IRD based on the moving average of the raw data. The moving average may be an exponential moving average or a simple moving average. Introducing a moving average serves to reduce the significance of false signals. From the moving average, the monitor device and/or the accessory device may determine/calculate the derivative, which emphasizes changes in the measured data points, i.e. changes in the resistance. The monitor device and/or the accessory device may determine/calculate the IRD from the derivative of the calculated moving average.

The IRD allows for a mathematical treatment and differentiation of leakage and moisture absorption. In particular, the IRD allows for the differentiation of leakage and expel of sweat. A threshold of 60%, of 70%, of 80%, or of 90% may be introduced to specify leakage. The threshold may be adaptive to the individual user, such that a lower or higher percentage may be used as the threshold to define a leakage. As an example, an IRD of 80% indicates an instant drop in resistance of 80%, which may indicate a sudden presence of output, i.e. a leakage. In case the threshold is set at 80%, the calculated IRD of more than, or equal to, 80% is considered leakage of output, whereas an IRD of less than 80% is considered moisture absorption, e.g. resulting from an excessive expel of sweat. Thus, the monitor device and/or the accessory device may determine whether a calculated IRD falls below or above a threshold value. The monitor device and/or the accessory device may be configured to generate a leakage signal if the calculated IRD is above the threshold value.

In the case of an electrode assembly divided into sensing zones, the above discussed mathematical process of differentiating a leakage from moisture absorption or expel of sweat may be applied to each sensing zone. Thus, the monitor device and/or the accessory device may be configured to determine/calculate the IRD for each of the one or more sensing zones of the base plate and/or sensor assembly part. Likewise, the derivative of the moving average may be used to monitor the health of the baser plate and/or the sensor assembly part by analysing the changes of resistance. Thus, the monitor device and/or the accessory device may be configured to apply the derivative to a forecast model for forecasting the health of the base plate and/or the sensor assembly part.

The wetted region, the wetted type, the moisture propagating direction, and/or the moisture propagating velocity may be used by the ostomy system, such as the monitor device, in determining a remaining usage time (e.g. time till replacement) of the base plate. The ostomy system, such as the monitor device, may be configured to provide a warning to the user based on the wetted region, the wetted type, the moisture propagating direction, and/or the moisture propagating velocity, e.g. such that the base plate may be replaced before the first adhesive layer detaches and/or detaches from the skin of the user.

The monitor device may be configured to generate a propagating moisture signal. The monitor device may be configured to generate a propagating moisture signal when any of the measured one or more resistances measured at one of the one or more sensing zones drops below a first trigger resistance value, and another of the measured one or more resistances measured at another of the one or more sensing zones, delayed by a time-value exceeding a threshold time-value, drops below a second trigger resistance value.

The propagating moisture signal may be indicative of a wetted region, e.g. the wetted region may include sensing zones where the measured resistances have dropped below trigger resistance values.

The wetted region may include regions between the sensing zones where the measured resistances have dropped below trigger resistance values.

The propagating moisture signal may be indicative of a moisture propagating direction. The moisture propagating direction may include a direction from one of the one or more sensing zones, where the measured resistance first dropped below the trigger resistance value, to another of the one or more sensing zones where the measured resistance next dropped below the trigger resistance value.

The propagating moisture signal may be indicative of a moisture propagating velocity. The moisture propagating velocity may be based on the distance between sensing zones and/or the time-delay between resistance drops. The moisture propagating velocity may be derived by dividing the distance between two of the one or more sensing zones that sequentially measured resistances dropping below trigger resistance values, by a time-delay between the measuring of the two resistance drops.

The first adhesive layer may be subjective to moisture content. For example, performance of the first adhesive layer may be affected by moisture content. The first adhesive layer may have an electrical conductivity that increases and an adhesive strength that decreases with increasing moisture content in the first adhesive layer. For example, electrical conductivity of the first adhesive layer may increase with increasing moisture content in the first adhesive layer. Alternatively or additionally, adhesive strength of the first adhesive layer may decrease with increasing moisture content in the first adhesive layer.

The plurality of electrodes may comprise at least one of metallic, ceramic, polymeric, and carbonaceous materials. For example, the plurality of electrodes may comprise metallic materials. Alternatively or additionally, the plurality of electrodes may comprise ceramic materials. Alternatively or additionally, the plurality of electrodes may comprise polymeric materials. Alternatively or additionally, the plurality of electrodes may comprise carbonaceous materials.

The plurality of electrodes may comprise one of silver and carbon. For example, the plurality of electrodes may comprise silver and/or carbon.

The base plate and/or the sensor assembly part may be at least one of bendable, flexible, twistable, and stretchable. For example, the base plate and/or the sensor assembly part may be bendable, flexible, twistable, and/or stretchable.

The ostomy system, such as the base plate and/or the sensor assembly part of the ostomy system, may further comprise a second adhesive layer, such as the second adhesive layer as described in more detail above. The second adhesive layer may be coupled to the distal surface of the first adhesive layer.

The second adhesive layer may be at least one of more adhesive, more moisture permeable, less moisture-absorbent, and lower in moisture capacity than the first adhesive layer. For example, the second adhesive layer may be more adhesive to the surface of the subject than the first adhesive layer. Alternatively or additionally, the second adhesive layer may be more moisture permeable than the first adhesive layer. Alternatively or additionally, the second adhesive layer may be less moisture-absorbent than the first adhesive layer. Alternatively or additionally, the second adhesive layer may have a lower moisture capacity than the first adhesive layer. The adhesive properties of the first and/or second adhesive layer may be selected to obtain desired sensing range, sensing responsiveness, adhesive security, and/or prolonged usable time of the base plate.

The base plate and/or the sensor assembly part may further comprise a first intermediate element, such as the first intermediate element as described in more detail above, e.g. between the first adhesive layer and the plurality of electrodes, such as a plurality of connection parts of the plurality of electrodes.

The first intermediate element may be less electrically conductive than the first adhesive layer. Additionally or alternatively, the first intermediate element may be less absorbing, e.g. water absorbing, than the first adhesive layer.

The ostomy system, such as the monitor device, may be configured to warn the user or prompt the user information regarding the "health" of the base plate. A healthy base plate may represent a base plate with low moisture content in the first adhesive layer and/or strong adhesive strength to the skin of the patient. An un-healthy base plate may represent a base plate with high moisture content in the first adhesive layer and weak adhesive strength to the skin of the patient. The health of the base plate may be determined based on the measured one or more resistances, e.g. because the one or more resistances are indicative of the moisture content in the first adhesive layer.

Also disclosed is a method of detecting moisture content in a base plate and/or the sensor assembly part of an ostomy system, such as the ostomy system as disclosed above.

The ostomy system comprises the base plate, and/or the sensor assembly part, and a monitor device. The base plate and/or the sensor assembly part include a first adhesive layer having a distal surface and a proximal surface, a plurality of electrodes disposed on the distal surface of the first adhesive layer, and one or more sensing zones each covering one of one or more regions of the first adhesive layer. The one or more sensing zones may include a first sensing zone, a second sensing zone and/or a third sensing zone. Each sensing zone includes two of the plurality of electrodes. The monitor device is electrically coupled to the plurality of electrodes of the base plate and/or the sensor assembly part.

The method comprises measuring one or more resistances in the one or more sensing zones via the plurality of electrodes. Each of the one or more resistances is measured between two of the plurality of electrodes at one of the one or more sensing zones.

The method further comprises determining moisture content of the first adhesive layer at each of the one or more sensing zones based on the measured one or more resistances.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 are typically adjusted by the user or nurse before application of the ostomy appliance to accommodate the user's stoma. The base plate may have a central region 400 and an outer region 404. The central region 400 is the region near the stomal opening 18 and/or substantially equal to the region within the coupling member 14. The outer region 404 is the region farther from the stomal opening 18 and/or substantially equal to the region outside of the coupling member 14.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
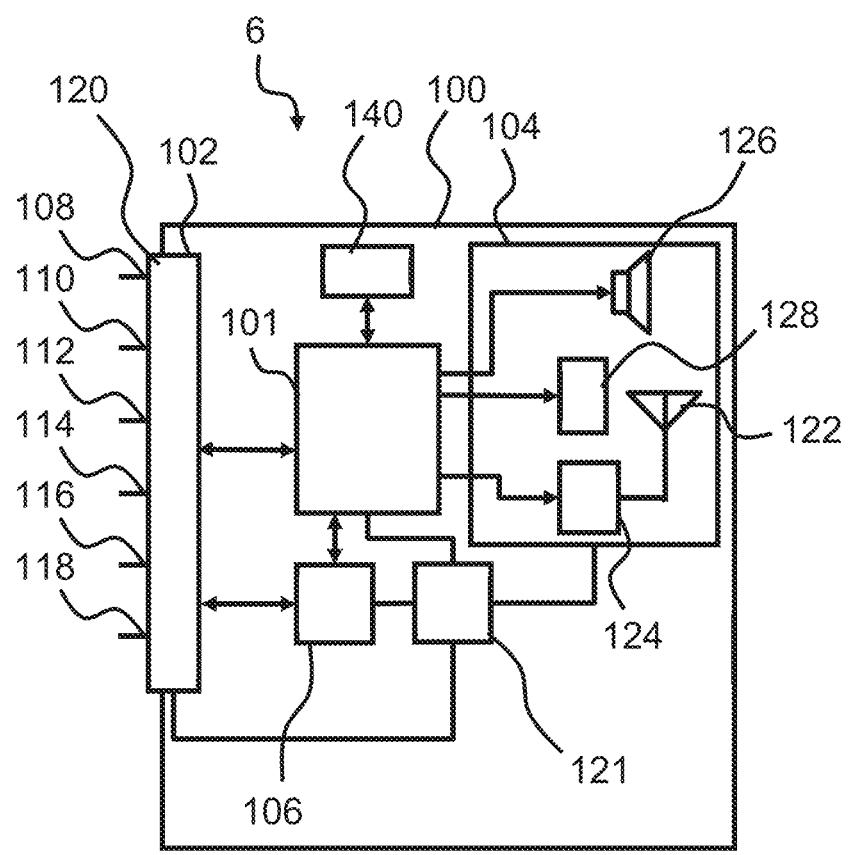
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory

106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. For example, the sensor unit 140 comprises a temperature sensor for feeding temperature data to the processor and/or a G-sensor or accelerometer for feeding acceleration data to the processor 101. Additionally and/or alternatively, the sensor unit 140 comprises a humidity sensor and/or an acoustic sensor. The sensor unit 140 may comprise alternative and/or additional sensors suitable and/or relevant to an ostomy system as described.

The processor 101 is configured to apply a processing scheme, and the first interface 102 is configured for collecting ostomy data from the base plate and/or the sensor assembly part coupled to the first interface, the ostomy data comprising first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part.

The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate and/or the sensor assembly part of the ostomy appliance based on one or more, e.g. all, of the first parameter data, the second parameter data and the third parameter data, wherein the operating state is indicative of a degree of radial erosion of the base plate and/or the sensor assembly part and/or acute leakage risk for the ostomy appliance. The monitor device 6 is configured to, in accordance with a determination that the operating state is a first operating state, transmit a first monitor signal comprising monitor data indicative of the first operating state of the base plate and/or the sensor assembly part via the second interface; and in accordance with a determination that the operating state is a second operating state, transmit a second monitor signal comprising monitor data indicative of the second operating state of the base plate and/or the sensor assembly part via the second interface.

Figure 3:
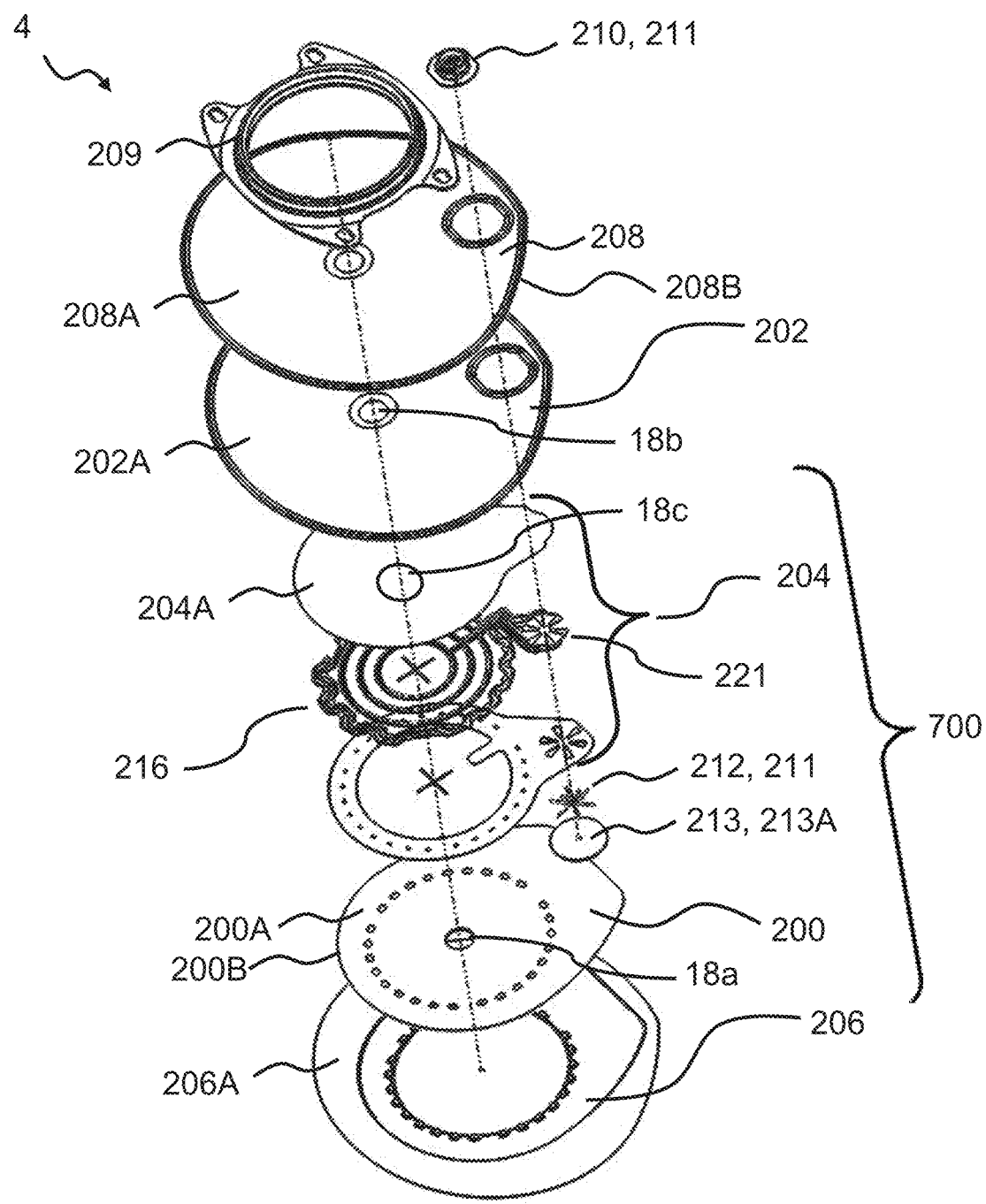
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

As illustrated in FIG. 3, the plurality of electrodes 216, which may be part of an electrode assembly 204 (see FIG. 4), may be arranged between the first and second adhesive layers 200, 202. Each of the first adhesive layer 200, second adhesive layer 202, and the electrode assembly 204 has a stomal opening 18a, 18b, 18c, respectively. The stomal openings 18a, 18b, 18c are aligned to define a stomal opening 18 of the base plate 4. The stomal opening 18 is configured to fit around the stoma of the user. In embodiments, at least one or more of the stomal openings 18a, 18b, 18c may be absent, thus requiring the missing opening(s) to be created before use (e.g. by the user).

In embodiments, the base plate 4 may comprise a top layer 208 disposed at least distally to the second adhesive layer 202 and/or first adhesive layer 200. The top layer 208 may provide protection to the rest of the base plate (e.g. except for the first connector 211 and the coupling ring 209) from being mechanically damaged (e.g. during handling and applying of the base plate 4) and/or chemically attacked (e.g. by the output, which may be acidic). A proximal surface 208B of the top layer 208 may be coupled to a distal surface 202A of the second adhesive layer 202. In embodiments, a distal surface 208A of the top layer 208 is substantially smooth thus prevents the base plate 4 from sticking to or damaging the clothing of the user.

According to embodiments, at least part of the base plate 4 may be bendable, flexible, twistable, and/or stretchable (e.g. by the user during base plate 4 application), e.g. to help improve coupling conformity and/or security of the adhesion between the base plate 4 and the surface of the user.

In embodiments, the first and second adhesive layers 200, 202 comprise hydrocolloid (e.g. cellulose, alginate) and polymer matrix (e.g. SIS) materials such that the adhesive layers 200, 202 are both adhesive to the surface of the subject (e.g. skin of the patient) and moisture absorbent (e.g. absorbent of the moisture of sweat and output), e.g. in addition to being at least one of bendable, flexible, twistable, and stretchable.

In embodiments, the first adhesive layer 200 and the second adhesive layer 202 comprise adhesive materials adhesive to each other, enabling the two adhesive layers 200, 202 be adhered by pressing them together with or without heating. In embodiments, the adhesive strength to the surface of the user may be reduced with increasing moisture content in the first and second adhesive layers 200, 202 while the electrical conductivity may increase with increasing moisture content in the first and second adhesive layers 200, 202.

In embodiments, the first adhesive layer 200 may have a smaller surface coverage than the second adhesive layer 202, while both the first and the second adhesive layers 200, 202 having bigger surface coverage than the plurality of electrodes 216 and the electrode assembly 204. Thereby, the plurality of electrodes 216 and the electrode assembly 204 may be encapsulated by adhesive, e.g. by the first adhesive layer 200 and the second adhesive layer 202.

For example, a proximal side 200B of the first adhesive layer 200 is configured to be attached to the skin of the patient and surround the stoma of the patient. The plurality of electrodes 216 and/or the electrode assembly 204, which may have a smaller surface coverage than the first adhesive layer 200, may be coupled to a distal side 200A of the first adhesive layer 200, leaving at least a rim portion of the distal surface 200A of the first adhesive layer 200 exposed. The second adhesive layer 202 may be distally coupled to the plurality of electrodes 216 or the electrode assembly 204 at a central region 400 (see FIG. 1) of the base plate 4. The second adhesive layer 202, which has larger surface coverage than the electrode assembly 204 and the plurality of electrodes 216, may further be distally coupled to the first adhesive layer 200 at least at the rim portion of the distal surface 200A of the first adhesive layer 200, leaving a rim portion of a proximal surface 202B of the second adhesive layer 202 exposed. The exposed rim of the proximal surface 202B of the second adhesive layer 202 may be configured to be attached to the skin of the patient at an outer region 404 (see FIG. 1) of the base plate 4 and surround the first adhesive layer 200. For example, the central region 400 of the base plate 4 may be substantially the same size as the electrode assembly 204 or the plurality of electrodes 216.

In embodiments, the difference in surface coverage between the first and second adhesive layers 200, 202 may be designed to feature the different adhesive properties of the first and second adhesive layers 200, 202. For example, the first adhesive layer 200 may possess higher moisture capacity and higher moisture absorbability than the second adhesive layer 202; whereas the second adhesive layer 202 may possess higher moisture permeability and higher adhesive strength to the surface of the subject than the first adhesive layer 202. In embodiments, adhesive properties of the first and second adhesive layers 200, 202 may be adjusted by adjusting the hydrocolloid-to-polymer compositional ratio. For example, increasing the hydrocolloid-to-polymer compositional ratio may increase moisture capacity and absorbability but may also decrease moisture permeability and adhesive strength to the surface of the subject.

In embodiments, the correlation between adhesive strength, moisture content, and electrical conductivity of the first adhesive layer 200 may be useful to how the ostomy system 1 may be configured to detect and/or estimate moisture content in the first adhesive layer 200, e.g. by measuring electrical conductivity, by way of measuring resistances between the plurality of electrodes 216. Through the moisture content detected and/or estimated, the ostomy system 1 may further provide information regarding to whether the first adhesive layer 200 has detached from the skin of the patient. More detailed description on moisture and leakage of output sensing is provided in later paragraphs.

In embodiments, the first adhesive layer 200, being disposed between the plurality of electrodes 216 and the skin of the patient, may be designed to have a higher moisture capacity than e.g. the second adhesive layer 202, e.g. to provide the ostomy system 1 with a larger sensing range in moisture content. The first adhesive layer 200 may also possess a higher moisture absorbability than e.g. the second adhesive layer 202, e.g. to help increase sensing responsiveness to changes in moisture content near the stoma of the user, which would also effectively reduce problems such as skin irritation and swelling, as well as pre-mature detachment of the first adhesive layer 200.

In embodiments, the second adhesive layer 202, being configured to be coupled to the skin of the patient at the outer region 404 of the base plate 4 surrounding the first adhesive layer 200, may be designed to have a higher adhesive strength to the skin of the patient than e.g. the first adhesive layer 200, e.g. to reduce risk of detachment of the base plate 4 from the skin of the patient. This helps the base plate 4 to stay attached to the skin of the patient even when the first adhesive layer 200 has completely detached from the surface of the patient. This provides extra protection against leakage of output undesirably exiting the containment of the ostomy appliance, such as the base plate 4. The second adhesive layer 202 may be further designed to have a higher moisture permeability than e.g. the first adhesive layer 200, e.g. to help the absorbed moisture in the second adhesive layer 202 to exit the second adhesive layer 202 quicker, e.g. to maintain sufficiently high adhesive strength to the surface, e.g. the skin of the patient. This further enhances the attachment security of the base plate on the skin of the patient.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
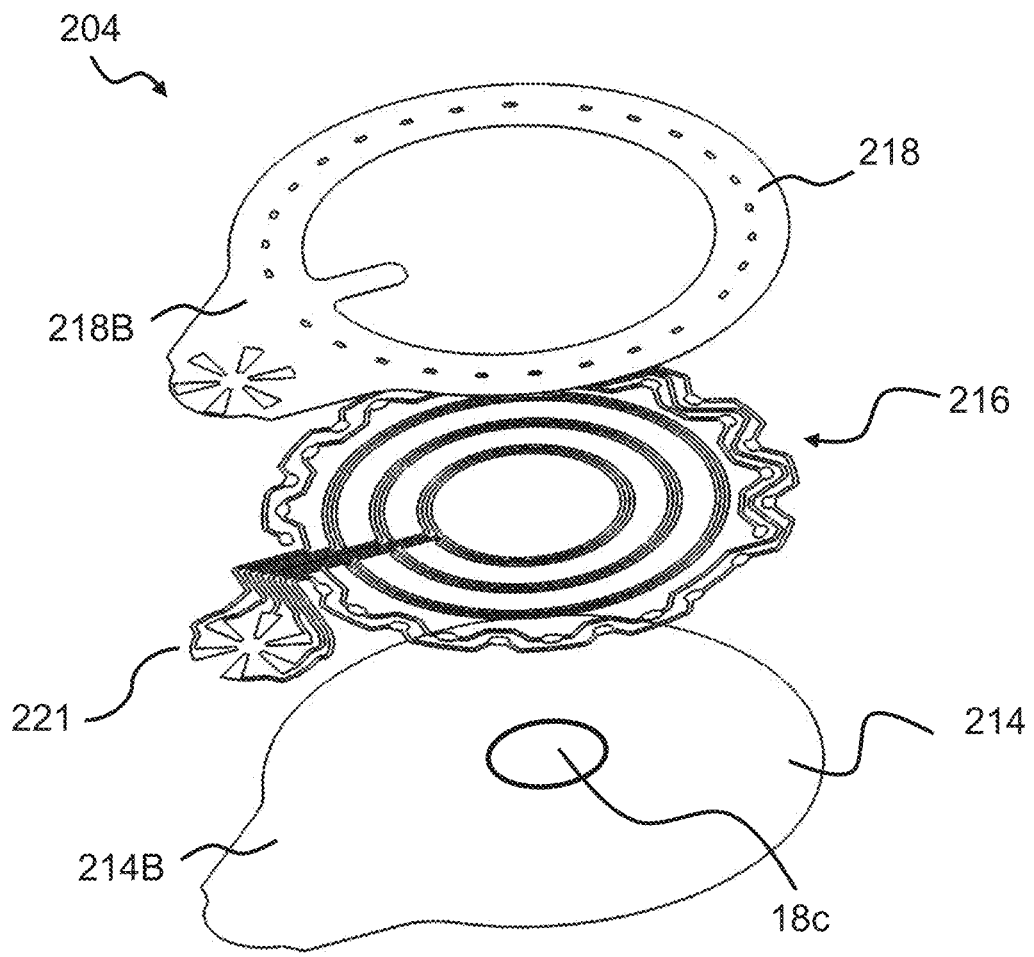
FIG. 4 is an exploded view of an exemplary electrode assembly.

FIG. 4 illustrates an exploded view of an exemplary electrode assembly 204 of a base plate and/or a sensor assembly part. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate and/or of the sensor assembly part. The masking element 218 covers or overlaps with parts of the electrodes 216 when seen in the axial direction.

In embodiments, the plurality of electrodes 216 may comprise at least one of metallic (e.g. silver, copper, gold, titanium, aluminium, stainless steel), ceramic (e.g. ITO), polymeric (e.g. PEDOT, PAN I, PPy), and carbonaceous (e.g. carbon black, carbon nanotube, carbon fibre, graphene, graphite) materials. The masking element may comprise at least one of polymeric (e.g. polyurethane, PTFE, PVDF) and ceramic (e.g. alumina, silica) materials.

In embodiments, the plurality of electrodes 216 may be prepared by screen-printing, inkjet-printing, direct-ink-writing, pen-plotting, 3D-printing, fused-deposition-modelling, contact-transfer printing, spray painting, chemical vapour depositing, physical vapour depositing, atomic-layer-depositing, wire-bending, and any other methods known to a person skilled in the art. The plurality of electrodes 216 may further require one of heat-curing, UV-curing, and oxygen-activating.

Figure 5:
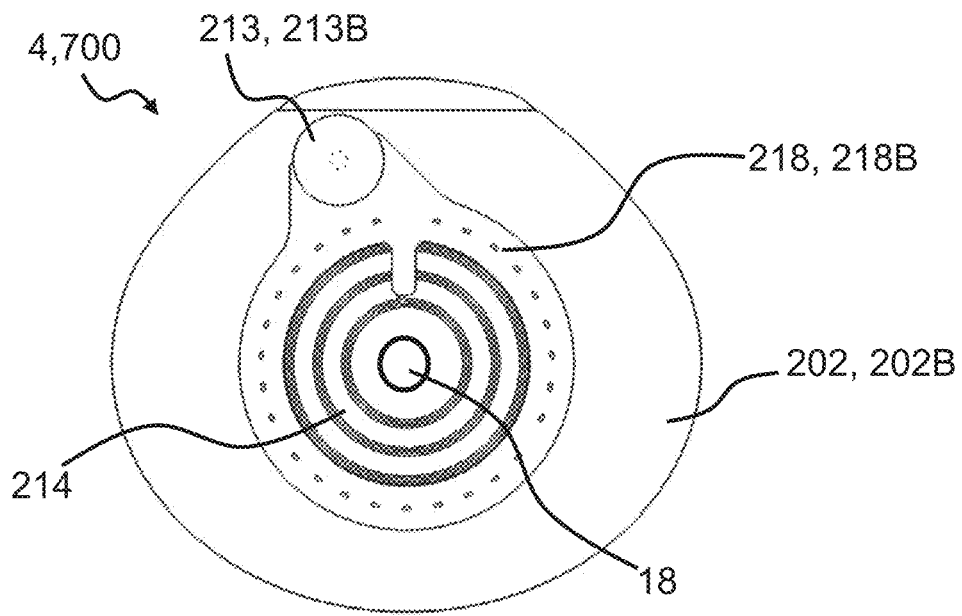
FIG. 5 is a proximal view of parts of a base plate and/or sensor assembly part.

FIG. 5 is a proximal view of proximal surfaces of base plate parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor assembly part.

In embodiments, the first intermediate element 213 may prevent the plurality of terminals 212 of the monitor interface from contacting the first adhesive layer 200 (see FIG. 3). In embodiments, the first intermediate element 213 has an electrical conductivity lower than that of the first adhesive layer 200 to avoid creating a less resistive pathway (e.g. through the first intermediate element 213) than through the first adhesive layer 200, e.g. in one or more of the one or more sensing zones 251 (see FIG. 11). Consequently, the connection parts 221, shielded by the first intermediate element 213, may be non-responsive to the increased electrical conductivity of the first adhesive layer 200 when moisture has been absorbed. This may help to more accurately measure moisture content at the one or more sensing zones 251 (see FIG. 11) by the plurality of electrodes 216. The first intermediate element 213 may also strengthen the structural integrity of the base plate 4 at least near the connection parts 221.

Figure 6:
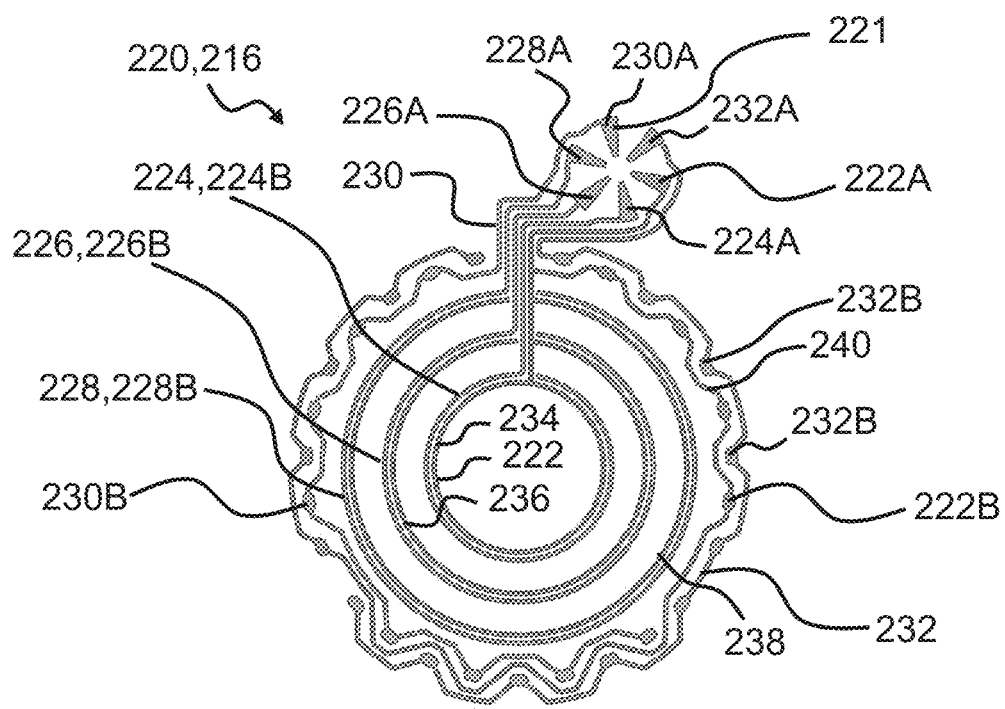
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The electrodes 216 comprises connection parts 221. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprises a fifth connection part 232A.

The fourth electrode 230 comprises fourth sensing parts 230B. The fifth electrode 232 comprises fifth sensing parts 232B.

In embodiments, the plurality of electrodes 216 may be configured to be used by the monitor device 6 of the ostomy system 1 to detect moisture content at each of the one or more sensing zones 261 (see FIG. 11), e.g. by way of measuring a resistance between two of the plurality of electrodes 216. This may be possible due to the correlation between electrical resistivity and moisture content of the first adhesive layer 200.

Figure 11:
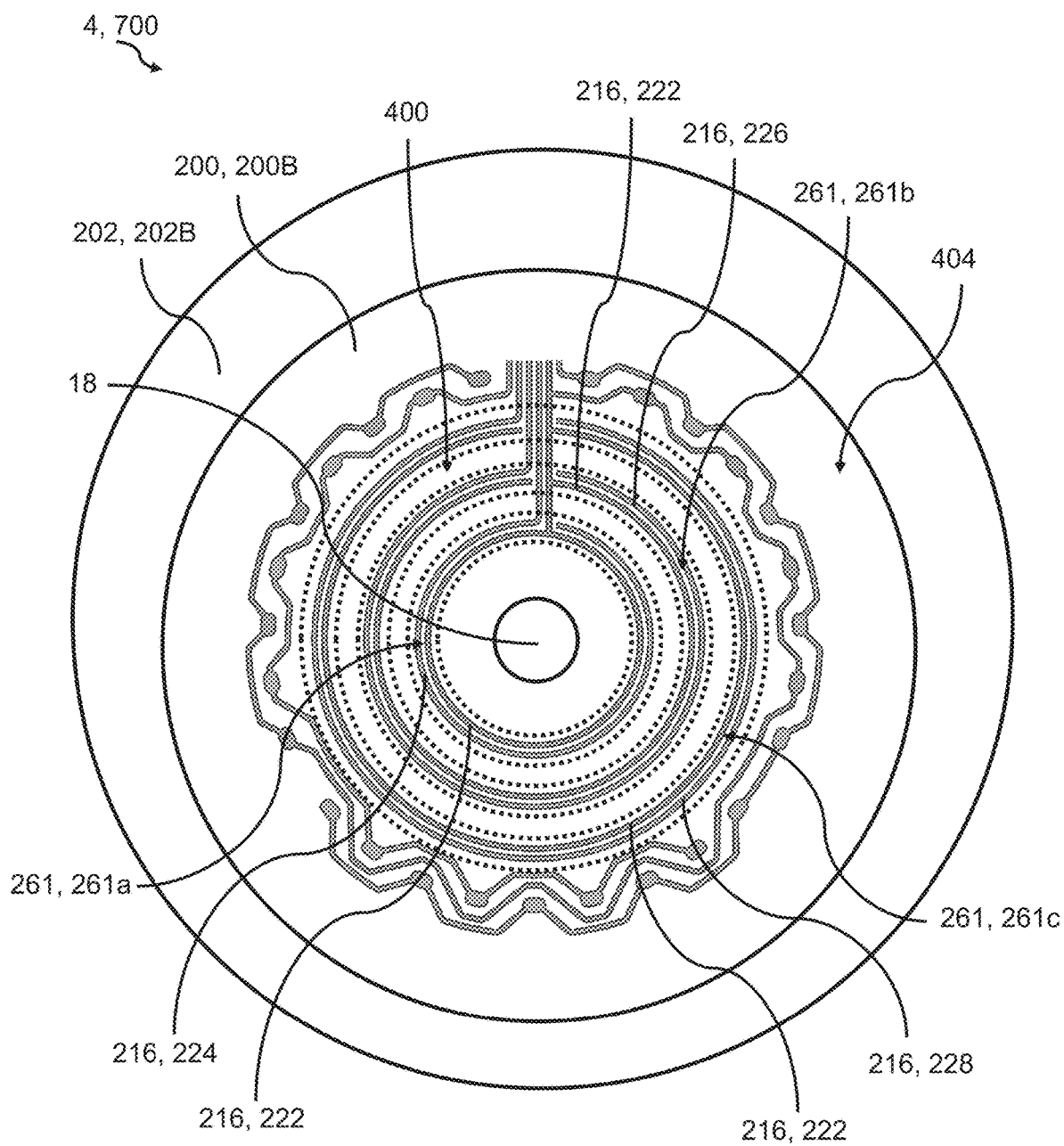
FIG. 11 is a proximal view of an exemplary base plate and/or sensor assembly part.

In embodiments, the ground sensing part 222B/first electrode part 234 of the ground electrode 222 may be substantially concentric to the first sensing part 224B of the first electrode 224, e.g. in the first sensing zone 261a of the one or more sensing zones 261 (see FIG. 11). Similarly, the ground sensing part 222B/second electrode part 236 of the ground electrode 222 may be substantially concentric to the second sensing part 226B of the second electrode 226, e.g. in the second sensing zone 261b of the one or more sensing zones 261 (see FIG. 11). Similarly, the ground sensing part 222B/third electrode part 238 of the ground electrode 222 may be substantially concentric to the third sensing part 228B of the third electrode 228, e.g. in the third sensing zone 261c of the one or more sensing zones 261 (see FIG. 11).

Figure 7:
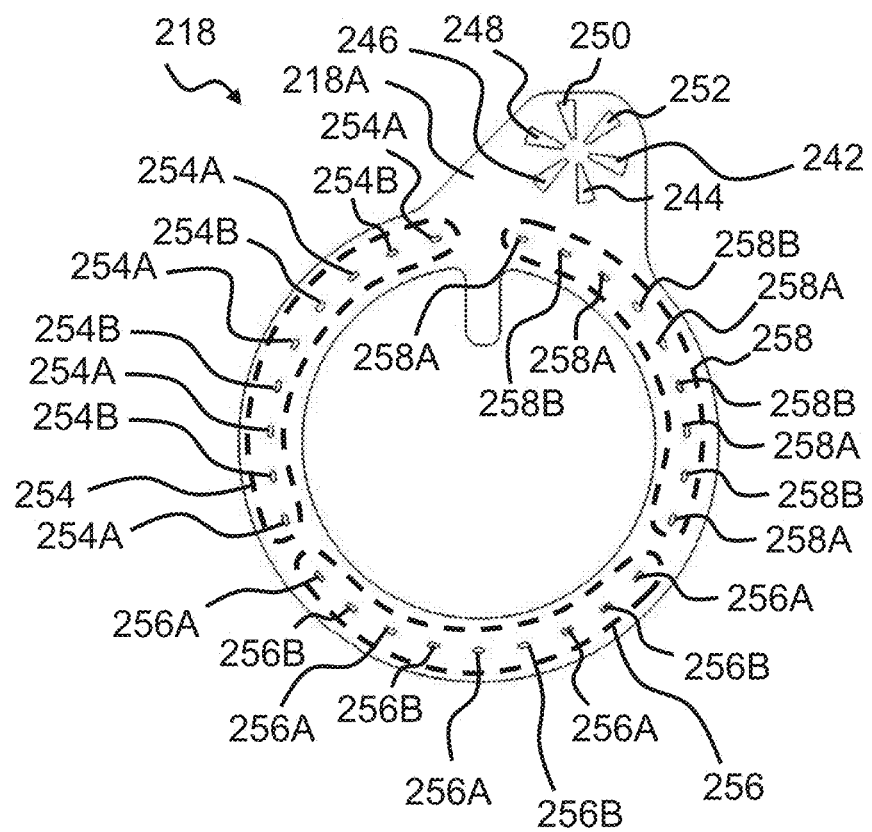
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
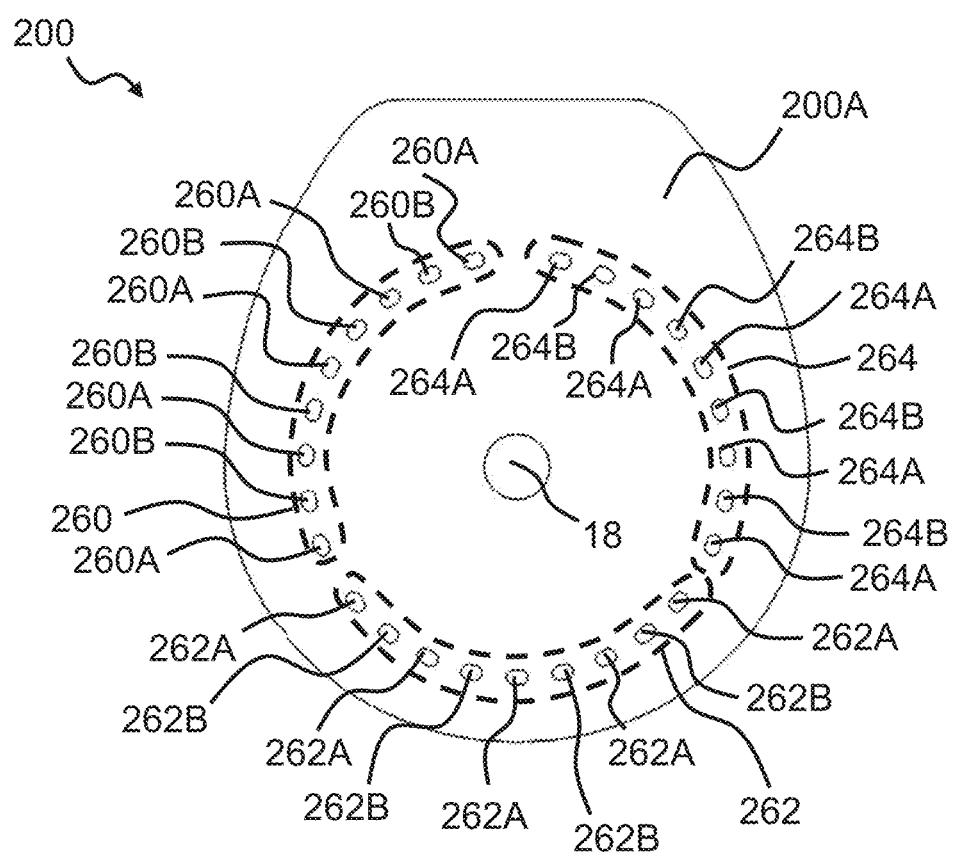
FIG. 8 is a distal view of an exemplary first adhesive layer.
Figure 9:
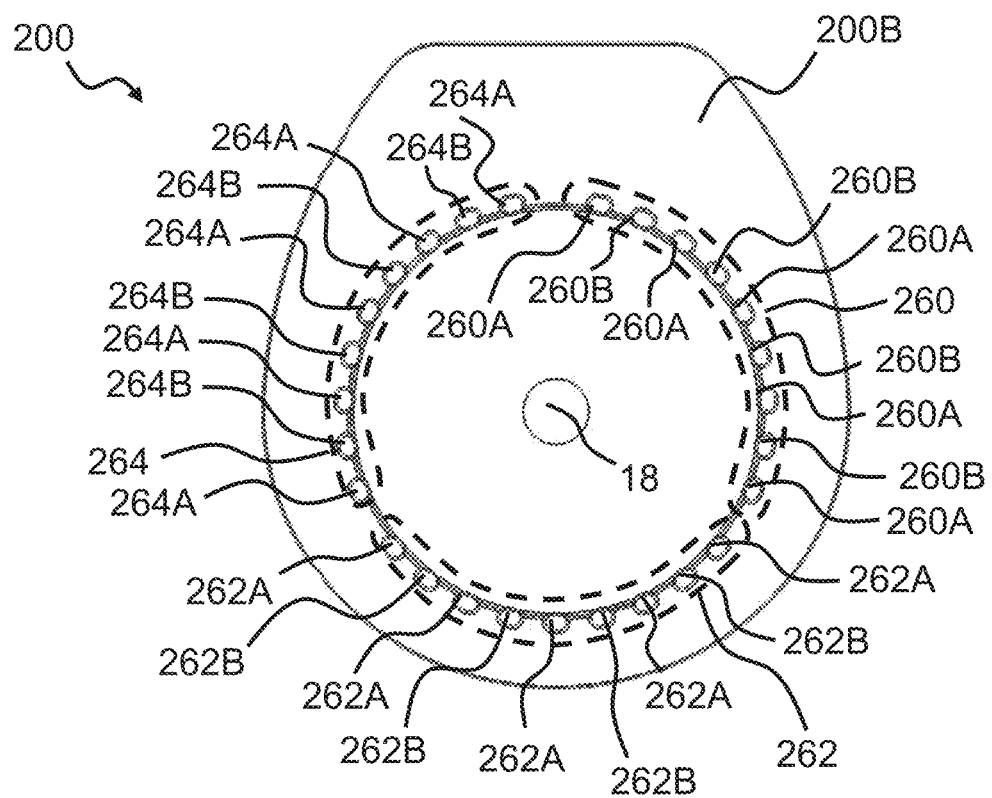
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
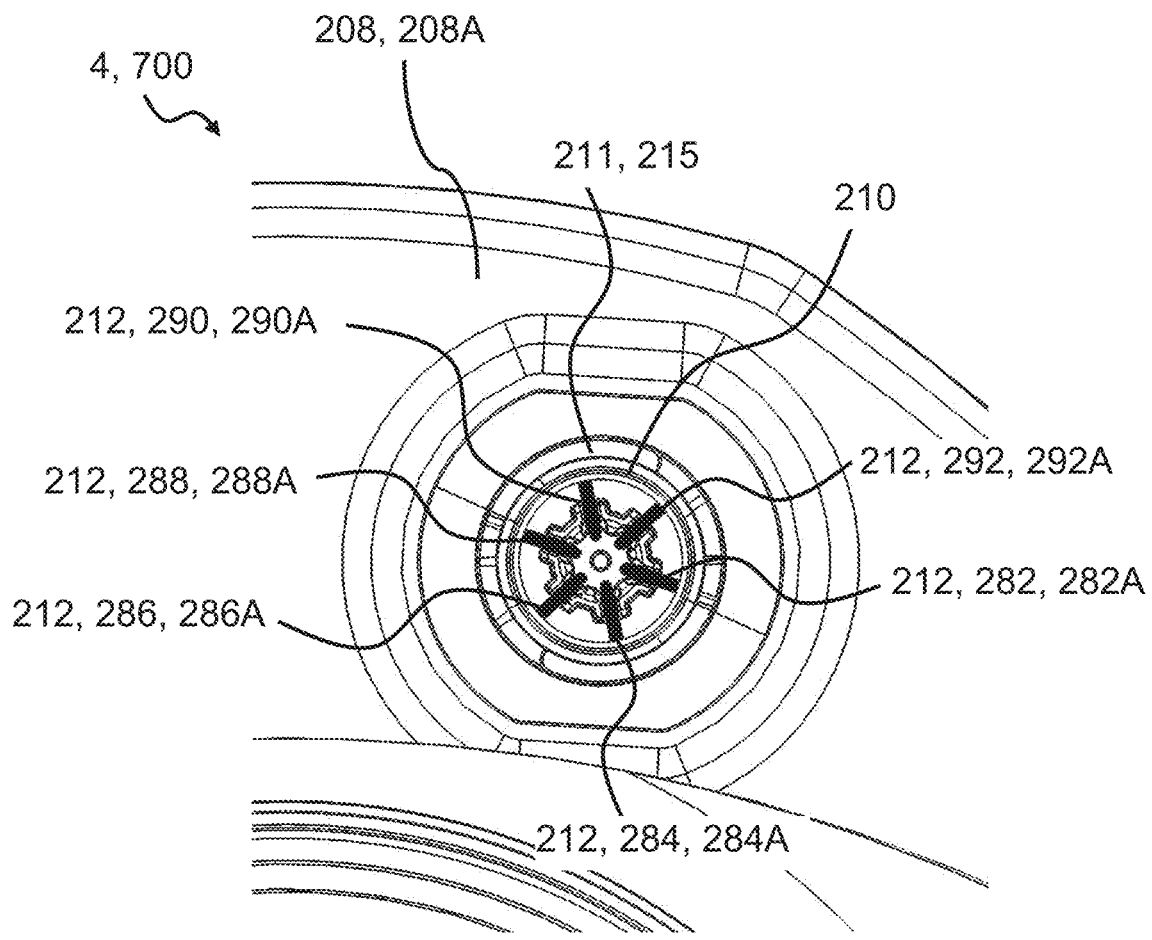
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

In reference to FIG. 1, FIG. 3, FIG. 6, and FIG. 10, the monitor interface 215 may include a plurality of terminals 212 and a coupling part 210. The plurality of terminals 212 may be configured to electrically couple the plurality of connection parts 221 of the plurality of electrodes 216 to the monitor device 6. The coupling part 210 may be configured to releasably and structurally couple the base plate 4 to the monitor device 6.

In reference to FIG. 3 and FIG. 10, the coupling part 210 may be distally attached or coupled to the top layer 208, which may be distally coupled to the first and/or second adhesive layers 200, 202 as described previously. The coupling between the coupling part 210 and the top layer 208 may be achieved by means including but not limited to: heat-bonding, mechanical fastening, solvent-bonding, UV-bonding, adhesive bonding, and/or ultrasonic welding.

FIG. 11 is a proximal view of an exemplary base plate 4. In embodiments, the base plate 4 and/or the sensor assembly part 700 may comprise one or more sensing zones 261 distributed at least one of concentrically about (as illustrated in FIG. 11 with three sensing zones), radially from (see FIG. 12), and/or angularly about (see FIG. 13) the central region 400 of the base plate 4 and/or the sensor assembly part 700.

The ostomy system 1 may be configured to detect the moisture content within the first adhesive layer 200 at each of the one or more sensing zones 261. In embodiments, the moisture content is detected by measuring a resistance at each of the one or more sensing zones 261 between two of the plurality of electrodes 216 (see FIG. 6) in each of the one or more sensing zones 261.

As will be described in greater detail, the ostomy system 1 (FIG. 1) may further be configured to detect a propagating moisture pattern in the first adhesive layer 200. Since the adhesive strength, moisture content, and electrical conductivity of the first adhesive layer 200 are correlated, thus enabling the ostomy system 1 to detect the moisture pattern by way of measuring resistances at the one or more sensing zones 261. The moisture pattern represents the regions in the first adhesive layer 200 where moisture content exceeds an amount that raises concerns for detachment of the first adhesive layer 200 from the skin of the patient. The moisture pattern may tend to propagate from the stoma near the stomal opening 18 at the central region 400 of the base plate 4 outwards to the outer region 404 of the base plate. For example, the moisture content in the output may often be high, causing moisture to enter into the first adhesive layer from the stomal opening 18 of the base plate 4. As the moisture continue to enter the first adhesive layer, one or more region of the first adhesive layer may become wetted, and the wetted region may continue to expand as a result of the moisture. For brevity, such an expanding wetted region will be denoted as the propagating moisture pattern. The propagating moisture pattern may include regions with higher moisture content (e.g. near the stomal opening 18) and regions with lower moisture content (e.g. near the outer region 404).

The adhesive strength of the first adhesive layer 200 may be reduced at elevated moisture content. Thus, when any of the resistance measured at any of the one or more sensing zones 261 is low enough (e.g. below a threshold and/or trigger resistance value) to indicate such elevated moisture content, the possibility of the first adhesive layer 200 being no longer adhered to the skin of the patient (i.e. detached) would increase. A detached first adhesive layer 200 increases the risk of leakage of output exiting the containment of the ostomy appliance 2, such as exiting the base plate 4. Therefore, the ostomy system 1 may be configured to warn the user or prompt the user information regarding the "health" of the base plate 4. A healthy base plate 4 may represent a base plate with low moisture content in the first adhesive layer 200 and strong adhesive strength to the skin of the patient, while resistances measured at the one or more sensing zones 261 being relatively high. Contrastly, an unhealthy base plate 4 may represent a base plate 4 with high moisture content in the first adhesive layer 200 and weak adhesive strength to the skin of the patient, while the resistances measured at the one or more sensing zones 261 being relatively low.

In embodiments, the concentric distribution of the one or more sensing zones 261, as illustrated in FIG. 11, helps the ostomy system 1 detect the propagating moisture pattern in the first adhesive layer 200 from the stoma at the central region 400 of the base plate 4 towards the outer region 404 of the base plate 4 in any direction within a base plane defined by the proximal surface 200B of the first adhesive layer 200. For example, a first sensing zone 261*a* of the one or more sensing zones 261 may be arranged on a first circle about the stomal opening 18 of the base plate 4, the first circle having a first radius, e.g. in the range from 10 mm to 20 mm, e.g. about 14 mm. For example, an inner electrode in the first sensing zone 261*a* may be arranged on the first circle. Similarly, a second sensing zone 261*b* of the one or more sensing zones 261 may be arranged on a second circle about the stomal opening 18 of the base plate 4, the second circle having a second radius e.g. in the range from 15 mm to 25 mm, e.g. about 20 mm. For example, an inner electrode in the second sensing zone 261*b* may be arranged on the second circle. Similarly, a third sensing zone 261*c* of the one or more sensing zones 261 may be arranged on a third circle about the stomal opening 18 of the base plate 4, the third circle having a third radius e.g. in the range from 20 mm to 30 mm, e.g. about 26 mm. For example, an inner electrode in the third sensing zone 261*a* may be arranged on the third circle. In embodiments, additionally at least a fourth sensing zone may be arranged concentrically about the central region 400 of the base plate 4. Additionally or alternatively, one or more sensing zones 261 may be distributed on ovals or polygons concentric about the stomal opening 18 of the base plate 4.

Figure 12:
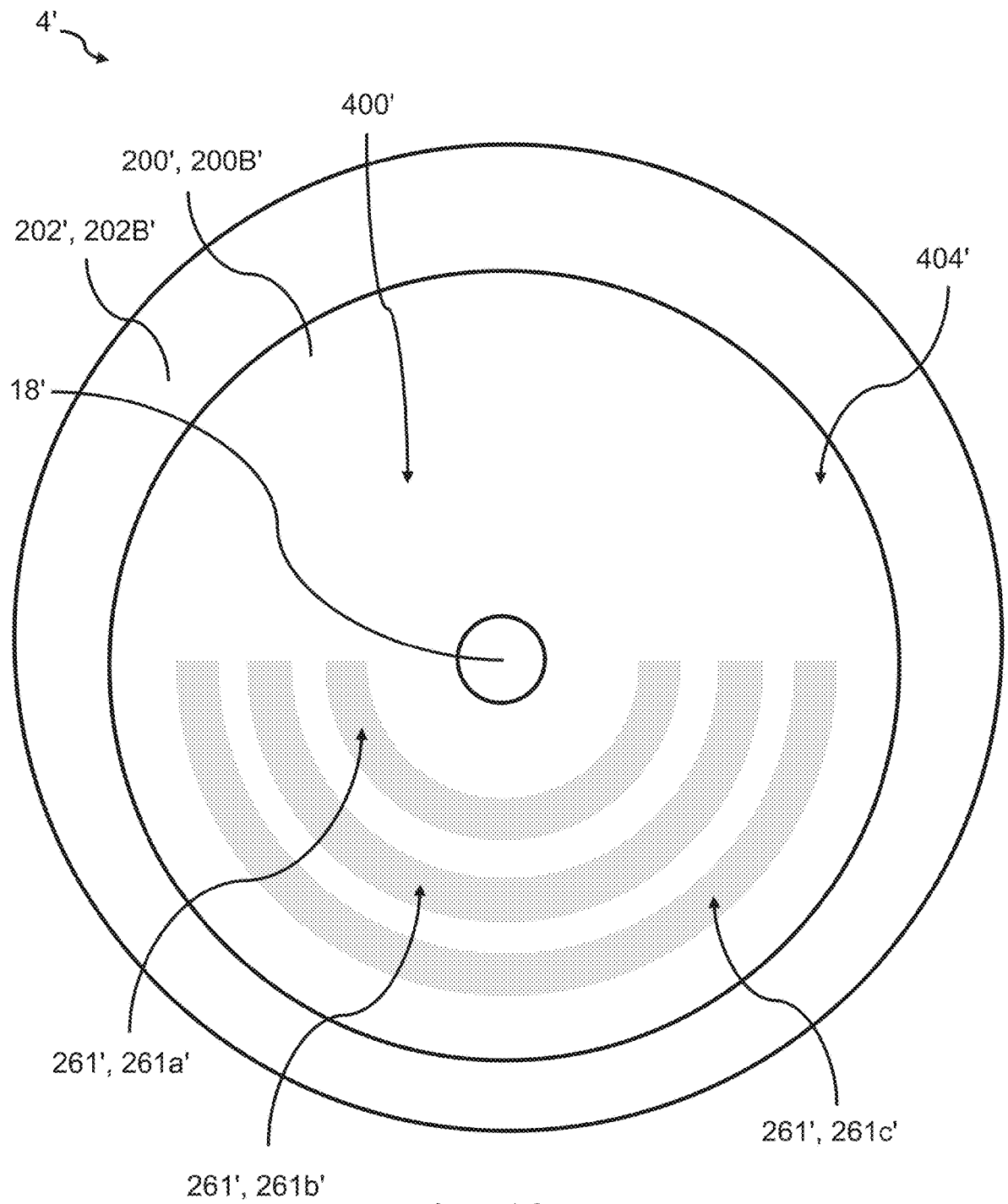
FIG. 12 illustrates sensing zones arranged radially.
Figure 13:
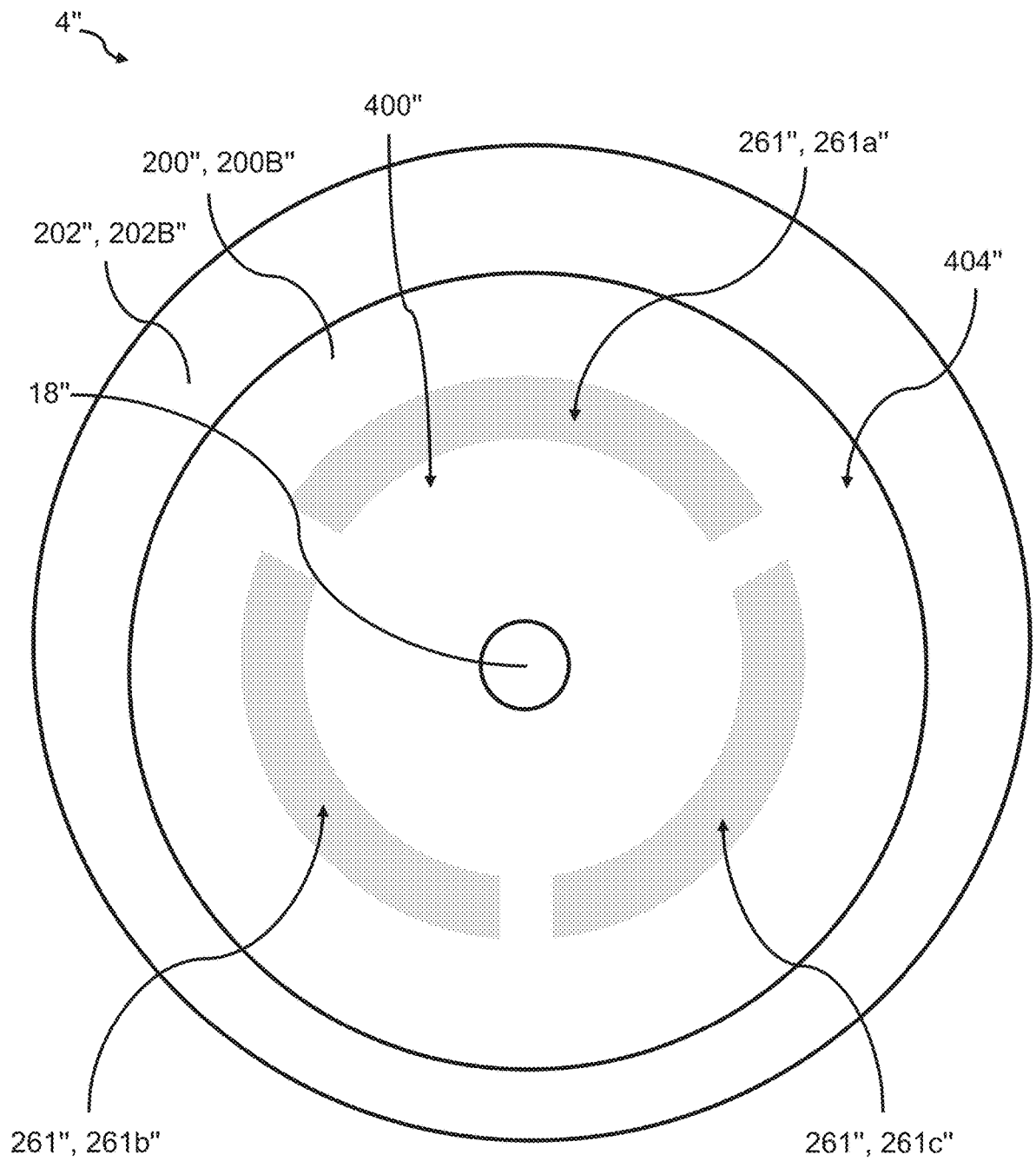
FIG. 13 illustrates sensing zones arranged concentrically.

Additionally or alternatively, the one or more sensing zones 261', 261" may be distributed radially from and/or angularly about the central region 400', 400" of the base plate 4', 4", as illustrated in FIGS. 12 and 13, e.g. to help detect the propagating moisture pattern from the central region 400', 400" towards the outer region 404', 404" of the base plate 4', 4".

FIG. 12 illustrates a base plate 4' with sensing zones arranged radially from the stomal opening 18' of the base plate 4' and outwards towards the outer region 404' of the base plate 4'. The radially arranged sensing zones 261', as illustrated in FIG. 12, may comprise a first sensing zone 261*a'* being disposed a first distance e.g. in the range from 10 mm to 20 mm, e.g. about 14 mm away from the center point of stomal opening 18'. For example, an inner electrode in the first sensing zone 261*b'* may be the first distance away from the stomal opening 18'. Similarly, a second sensing zone 261*b'* may be disposed a second distance e.g. in the range from 15 mm to 25 mm, e.g. about 20 away from the center point of stomal opening 18'. For example, an inner electrode in the second sensing zone 261*b'* may be the second distance away from the stomal opening 18'. Similarly, a third sensing zone 261*c'* may be disposed a third distance e.g. in the range from 20 mm to 30 mm, e.g. about 26 mm away from the center point of stomal opening 18'. For example, an inner electrode in the third sensing zone 261*b'* may be the third distance away from the stomal opening 18'. Furthermore, FIG. 12 also illustrates that the sensing zones may span a limited angle space, such as an angle space of, e.g., 180 degrees. Furthermore, in the illustrated example, the three sensing zones span the same angle space.

FIG. 13 illustrates a base plate 4" with sensing zones arranged angularly about the stomal opening 18" of the base plate 4". The angularly arranged sensing zones 261", as illustrated in FIG. 13, may comprise a first sensing zone 261*a"* being disposed on a circle from 0 to 120 degrees about the stomal opening 18" of the base plate 4", e.g. spanning an angle space of approximately 120 degrees. Similarly, a second sensing zone 261*b"* may be disposed on the circle from 120 degrees to 240 degrees about the stomal opening 18" of the base plate 4''', e.g. spanning an angle space of approximately 120 degrees.

Similarly, a third sensing zone 261*c"* may be disposed on the circle from 240 to 360 degrees about the stomal opening 18" of the base plate 4''', e.g. spanning an angle space of approximately 120 degrees.

In embodiments, each of the one or more sensing zones 261 includes a unique region of the first adhesive layer 200 that is different from any other of the one or more sensing zones 261. The regions included in the one or more sensing zones 261 may overlap but not in totality. For example, 50% of a first region which the first sensing zone 261*a* includes may overlap with a second region included in the second sensing zone 261*b*, while the remaining 50% of the first region overlaps with no other regions included in any of the one or more sensing zones 261. Thus, any of the one or more sensing zones 261 may be different from any other of the one or more sensing zones 261.

As will be described in greater detail, the known locations of the one or more sensing zones 261 may further be used by the ostomy system 1 in determining a propagation direction and a propagation velocity of the propagating moisture pattern.

In embodiments, each of the one or more sensing zones 261 includes at least the sensing parts (see FIG. 6) of two of the plurality of electrodes 216 such that each of the one or more sensing zones 261 may be generally defined, outlined, designated, or specified by two of the plurality of electrodes 216. For example, the ground and first of the plurality of electrodes 222, 224 may define the first sensing zone 261a. The first electrode 224 and the second electrode 226 of the plurality of electrodes 216 may define the second sensing zone 261b. The ground electrode 222 and the third electrode 228 of the plurality of electrodes 216 may define the third sensing zone 261c. In embodiments, at least one of the plurality of electrodes 216 may be in more than one of the one or more sensing zones 261 (e.g. the ground electrode 222). Additionally, the first electrode 224 of the plurality of electrodes may form a fourth, and/or fifth sensing zones with the second and/or third electrodes 224, 226, respectively. In embodiments, three or more of the plurality of electrodes 216 may be in one of the one or more sensing zone 261 such that two or more resistances are measured across any two of the three or more of the plurality of electrodes 216, which in combination indicate the moisture content in the corresponding sensing zone 261.

At least portions of the sensing parts of the plurality of electrodes 216 may extend at least three-quarters of the circumferences of their corresponding concentric circles. Additionally or alternatively, at least portions of the sensing parts of the plurality of electrodes 216 may extend less than full circles to form open loops on their corresponding concentric circles.

In addition to detecting moisture content in the first adhesive layer 200 at the one or more sensing zones 261, the monitor device 6 of the ostomy system 1 may be further configured to generate a wetted signal when the moisture level has been determined, based on the measured resistance, to have increased in at least one of the one or more sensing zones 261. The wetted signal may be indicative of a sensing zone location and the moisture content measured at the corresponding sensing zone. In embodiments, the moisture content at each of the one or more sensing zones 261 is continuously monitored and recorded by the ostomy system 1. In other embodiments, the moisture content at each of the one or more sensing zones 261 is continuously monitored while only recorded by the ostomy system 1 when the wetted signal has been generated, which may decrease power consumption and prolong device runtime.

As described previously, the ostomy system 1 may be configured to, by measuring resistances across the plurality of electrodes 216 at each of the one or more sensing zones 261 in the base plane 4, detect the propagating moisture pattern.

Figure 14:
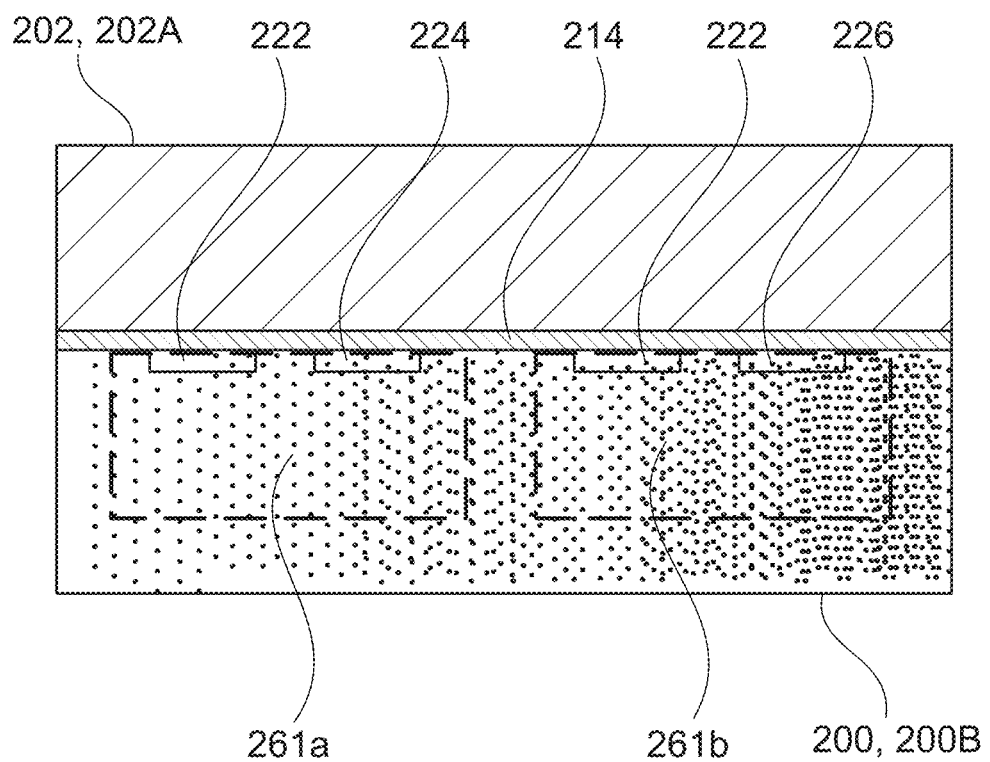
FIG. 14 is a cross-sectional view of an exemplary base plate and/or sensor assembly part of the ostomy system.

FIG. 14 is a cross-sectional view of an exemplary base plate 4 (as illustrated in FIG. 11) showing the propagating moisture pattern in the first adhesive layer 200. In embodiments, the ostomy system 1 may be configured to detect the moisture pattern propagating from the stoma at the stomal opening 18 of the base plate 4 outwards to the outer region 404 of the base plate 4 (see FIG. 11). For example, the concentric arrangement (FIG. 11) of the one or more sensing zones 261 may help the ostomy system 1 to first detect the propagating moisture pattern in the first sensing zone 261a, causing the monitor device 6 to measure, through the ground and first of the plurality of electrodes 222, 224, a drop in resistance to less than a first trigger resistance indicative of the increased level of moisture content in the first adhesive layer 200 at the first sensing zone 261a. The elevated moisture content in the first sensing zone 261a is illustrated as the heavily dotted region in the first adhesive layer near the right side of the FIG. 14. The concentric arrangement of the one or more sensing zones 261 may further help the ostomy system 1 to next detect the propagating moisture pattern in the second sensing zone 261b, causing the monitor device 6 to measure, through the ground and second of the plurality of electrodes 222, 226, a drop in resistance to less than a second trigger resistance indicative of the increased level of moisture content in the first adhesive layer 200 at the second sensing zone 261b. A first time-delay may exist, and be measured, between the detection of the first drop in resistance at the first sensing zone 261a and the second drop in resistance at the second sensing zone 261b. In embodiments, the ostomy base plate comprises at least a third sensing zone 261c to detect the propagating moisture pattern further outwards from the stomal opening 18 towards the outer region 404 of the base plate 4.

Figure 15:
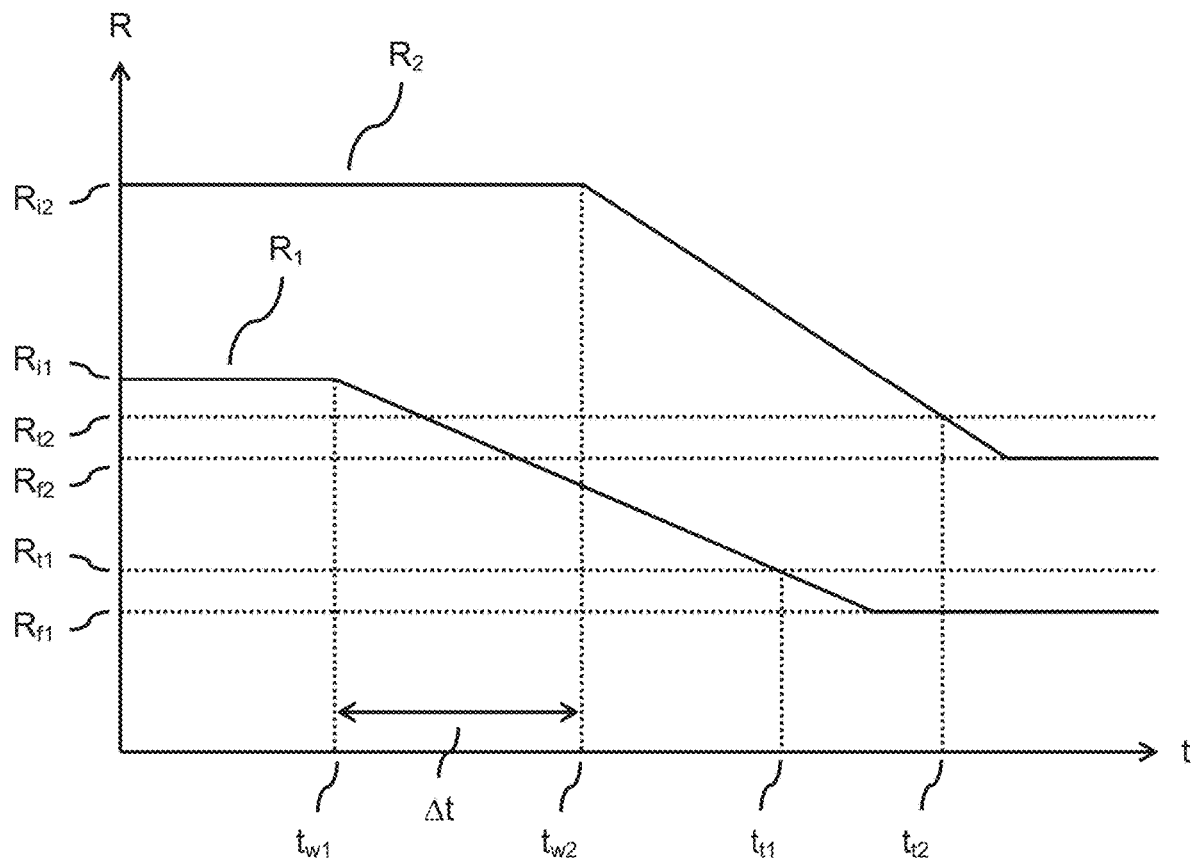
FIG. 15 illustrates an exemplary resistance measurement.

FIG. 15 is a diagram illustrating exemplary resistance measurements.

A first resistance $R_1$ is measured in a first sensing zone. The first resistance $R_1$ may be measured between a ground electrode and a first electrode of the plurality of electrodes. As shown, the first resistance $R_1$ measured in the first sensing zone, before moisture content increases, substantially equals to a first primary resistance value $R_{i1}$. The first primary resistance value $R_{i1}$ has a relatively high value and represents the relatively high electrical resistivity of the first adhesive layer between the two electrodes used by the monitor device of the ostomy system for resistance measurement at the first sensing zone. As illustrated in FIG. 15, the first resistance $R_1$ starts to drop from the first primary resistance value $R_{i1}$ to about a first secondary resistance value $R_{f1}$ when the moisture pattern enters the first sensing zone and increases moisture content at time $t_{w1}$. The first secondary resistance value $R_{f1}$ has a relatively low value and represents the reduced electrical resistivity of the first adhesive layer due to increased moisture content.

A second resistance $R_2$ is measured in a second sensing zone. The second resistance $R_2$ may be measured between the ground electrode and a second electrode of the plurality of electrodes. As shown, the second resistance $R_2$ measured in the second sensing zone, before moisture content increases, substantially equals to a second primary resistance value $R_{i2}$. The second primary resistance value $R_{i2}$ has a relatively high value and represents the relatively high electrical resistivity of the first adhesive layer between the two electrodes used by the monitor device of the ostomy system for resistance measurement of the second sensing zone. As illustrated in FIG. 15, the second resistance $R_2$ starts to drop from the second primary resistance value $R_{i2}$ to about a second secondary resistance value $R_{f2}$ when the moisture pattern propagates beyond the first sensing zone and enters the second sensing zone and increases moisture content at time $t_{w2}$. The second secondary resistance value $R_{f2}$ has a relatively low value and represents the reduced electrical resistivity of the first adhesive layer due to increased moisture content.

As illustrated in FIG. 11, the first sensing zone 261a may be nearer to the stomal opening 18 than the second sensing zone 261b. Thus, the drop in resistance in the second sensing zone 261b may be delayed by a first time-value from the drop the in resistance in the first sensing zone 261a to reflect the moisture pattern propagating from the stomal opening 18 outwards to the outer region 404 of the base plate 4 (see FIG. 1). When the first resistance $R_1$ measured in the first sensing zone 261a drops below the first trigger resistance value $R_{t1}$, e.g. at time $t_{t1}$, followed by the second resistance value $R_2$ measured in the second sensing zone 261b dropping below the second trigger resistance value $R_{t2}$, e.g. at time $t_{t2}$, the ostomy system may be configured to generate a propagating moisture signal, e.g. at time $t_{t2}$, to indicate the moisture pattern has propagated to the first and second sensing zones consecutively.

In embodiments, the propagating moisture signal may be indicative of at least one of wetted region, moisture propagating direction, and moisture propagating velocity. The wetted region may comprise the sensing zones where resistances have measured to be lower than the trigger resistance values. Additionally, the leakage location may comprise the regions between the sensing zones where resistances have measured to be lower than the trigger resistance values.

In embodiments, the moisture propagating direction may comprise a direction from one of the one or more sensing zones 261 that first measured a resistance dropping below trigger resistance value, to another of the one or more sensing zones 261 that next measured a resistance dropping below trigger resistance value. The moisture propagating direction may be substantially parallel to the proximal surface 200B of the first adhesive layer 200. The moisture propagating velocity may be derived by dividing the distance between the two sensing zones that sequentially measured resistances dropping below trigger resistance values, by a time-delay between the measuring of two resistance drops at the two sensing zones (see FIG. 15, $\Delta t = t_{w2} - t_{w1}$). The time-delay may be a delay by a first time-value that exceeds a threshold time-value.

In embodiments, the moisture propagating velocity derived may help the ostomy system 1, such as the monitor device, in determining a remaining usage time (e.g. time till replacement) of the base plate 4. For example, from the known locations of the sensing zones, the size of the first adhesive layer 200, adhesive properties (e.g. adhesive strength), and the derived moisture propagating velocity, the ostomy system 1 may be configured to determine the remaining time until the propagating moisture pattern spreads to substantial portions (or substantially near the outer region 404 of the base plate 4) of the first adhesive layer 200. The ostomy system 1 may be configured to provide warning to the user such that the base plate 4 may be replaced before the first adhesive layer unintended detaches from the skin of the user due to greatly reduced adhesive strength between the base plate 4 and the skin of the user. Such a prediction would not only help prevent unintended detachment of the base plate 4, but may also reduce the time of contact between the wetted first adhesive layer 200 and the skin of the user by indicating the base plate 4 may be due for replacement or cleaning. The described warning may reduce skin problems such as irritation or swelling.

In reference to FIG. 15, the first derivative (slope) of the resistance drop as a function of time, e.g. the rate of change of the resistance, may be correlated to the diffusion rate of moisture in the first adhesive layer 200. Additionally, the slope may provide information as to the quantity of moisture entering the corresponding sensing zone. For example, a steep slope may suggest that the propagating moisture pattern has entered a larger percentage (e.g. 80%) of the first adhesive layer 200 within the sensing zone of interest. Contrastly, a gradual slope may suggest that the propagating moisture pattern has entered a smaller percentage (e.g. 20%) of the first adhesive layer 200 within the sensing zone of interest. Furthermore, rate of change may be indicative of whether the underlying cause of the detected increased moisture content. For example, a big rate of change may be indicative of output causing the moisture increase, while a smaller rate of change may be indicative of sweat causing the moisture increase.

Figure 16:
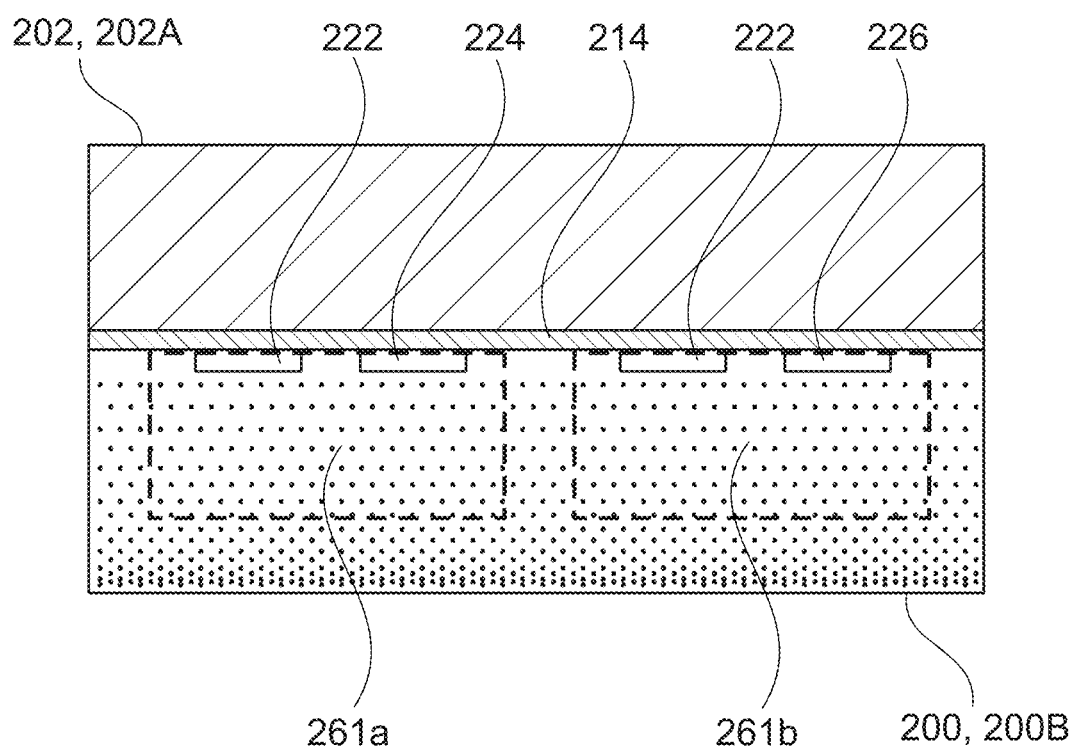
FIG. 16 is a cross-sectional view of an exemplary base plate and/or sensor assembly part of the ostomy system.

FIG. 16 is a cross sectional view of a collectively wetted base plate 4 of an ostomy system 1, in accordance with various embodiments of the disclosure. Through detecting and/or estimating moisture content, the ostomy system may further be configured to detect a collectively wetted base plate. A collectively wetted base plate 4 may be a base plate 4 that has absorbed moisture substantially uniformly and with the same moisture content in at least the majority of the one or more sensing zones 261a, 261b. Such a collectively wetted base plate 4 may have been wetted by sweat of the user which may be substantially generated by the skin under the first adhesive layer 200 of the base plate 4.

For example, in a collectively-wetted base plate 4, as illustrated in FIG. 16, the moisture contents in the first sensing zone 261a and in the second sensing zone 261b may be substantially the same, as indicated by the resistances measured using the ground electrode 222 and the first electrode 224 in the first sensing zone 261a and the ground electrode 222 and the second electrode 226 in the second sensing zone 261b. When the thickness of the first adhesive layer 200 is about constant, the distances from the proximal surface 200B of the first adhesive layer, which would be in contact with the skin generating sweat, to the one or more sensing zones are about the same. When the moisture diffuses at relatively the same rate across all regions in the first adhesive layer 200, the moisture content in each of the one or more sensing zones 261 would substantially increase at the same rate and to the same moisture content. The first adhesive layer 200 of a collectively-wetted base plate 4 may have regions of higher moisture content (e.g. near the proximal surface 200B, illustrated as having many dots) and regions of lower moisture content (e.g. near the plurality of electrodes 216, illustrated as having fewer dots relative to the high moisture content-situation), reflecting the source of the moisture being the skin at the proximal surface 200B of the first adhesive layer 200.

Figure 17:
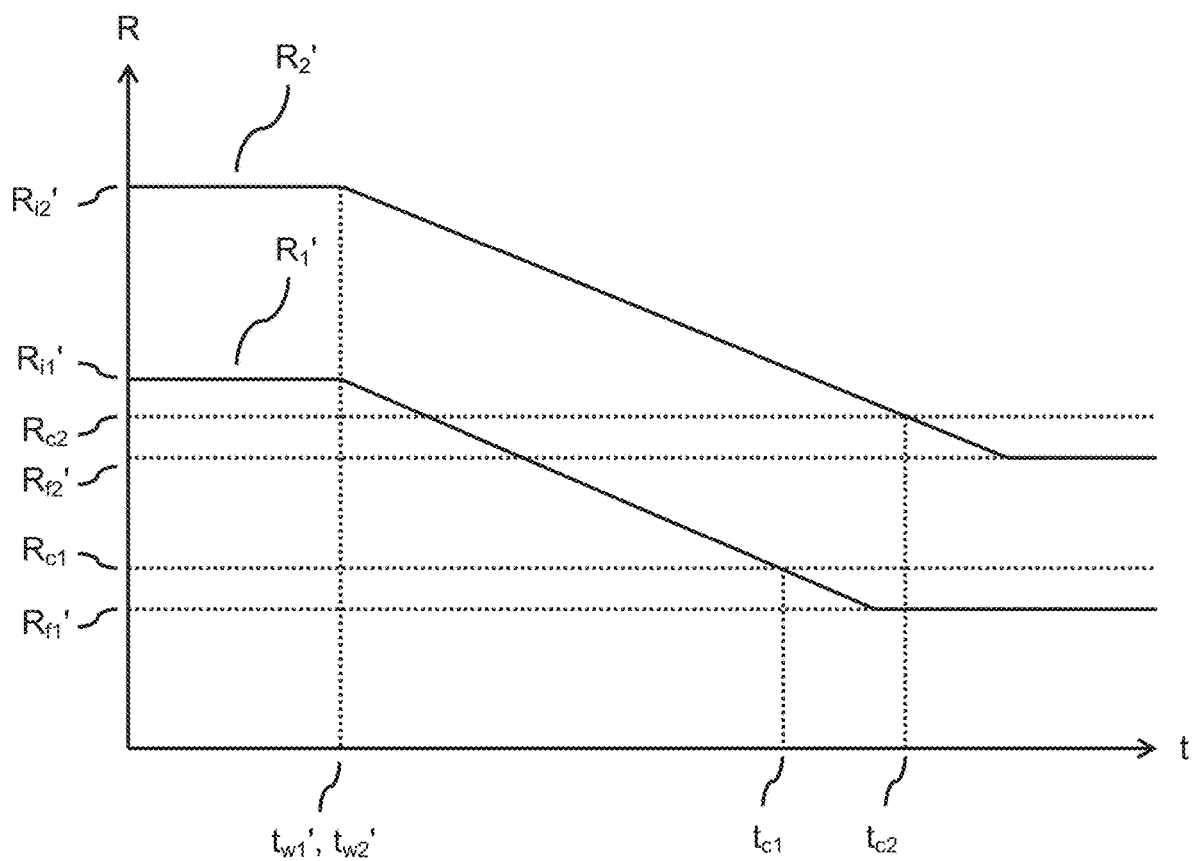
FIG. 17 illustrates an exemplary resistance measurement.

FIG. 17 is a diagram illustrating exemplary resistance measurements.

A first resistance $R_1'$ is measured in a first sensing zone. The first resistance $R_1'$ may be measured between a ground electrode and a first electrode of the plurality of electrodes. As shown, the first resistance $R_1'$ measured in the first sensing zone, before moisture content increases, substantially equals to a first primary resistance value $R_{i1}'$. The first resistance $R_1'$ starts to drop from the first primary resistance value $R_{i1}'$ to about a first secondary resistance value $R_{f1}'$ when the moisture pattern enters the first sensing zone and increases moisture content at time $t_{w1}'$.

A second resistance $R_2'$ is measured in a second sensing zone. The second resistance $R_2'$ may be measured between a ground electrode and a second electrode of the plurality of electrodes. As shown, the second resistance $R_2'$ measured in the second sensing zone, before moisture content increases, substantially equals to a second primary resistance value $R_{i2}'$. The second resistance $R_2'$ starts to drop from the second primary resistance value $R_{i2}'$ to about a second secondary resistance value $R_{f2}'$ when the moisture pattern enters the second sensing zone and increases moisture content at time $t_{w2}'$.

The substantially identical start times $t_{w1}'$, $t_{w2}'$ of the resistance drops in the two sensing zones 261a, 261b indicate a collectively-wetted base plate 4, as opposed to a base plate 4 having a propagating moisture pattern (FIG. 14 and FIG. 15) with a characteristic time-delay $\Delta t$ between detection of resistance drops. When the resistances measured $R_1'$, $R_2'$ in the sensing zones drop below the threshold resistance values, e.g. $R_{c1}$, $R_{c2}$), e.g. at times $t_{c1}$, $t_{c2}$, the monitor device 6 of the ostomy system 1 may be configured to generate a collectively-wetted signal, e.g. at time $t_{c2}$.

Figure 18:
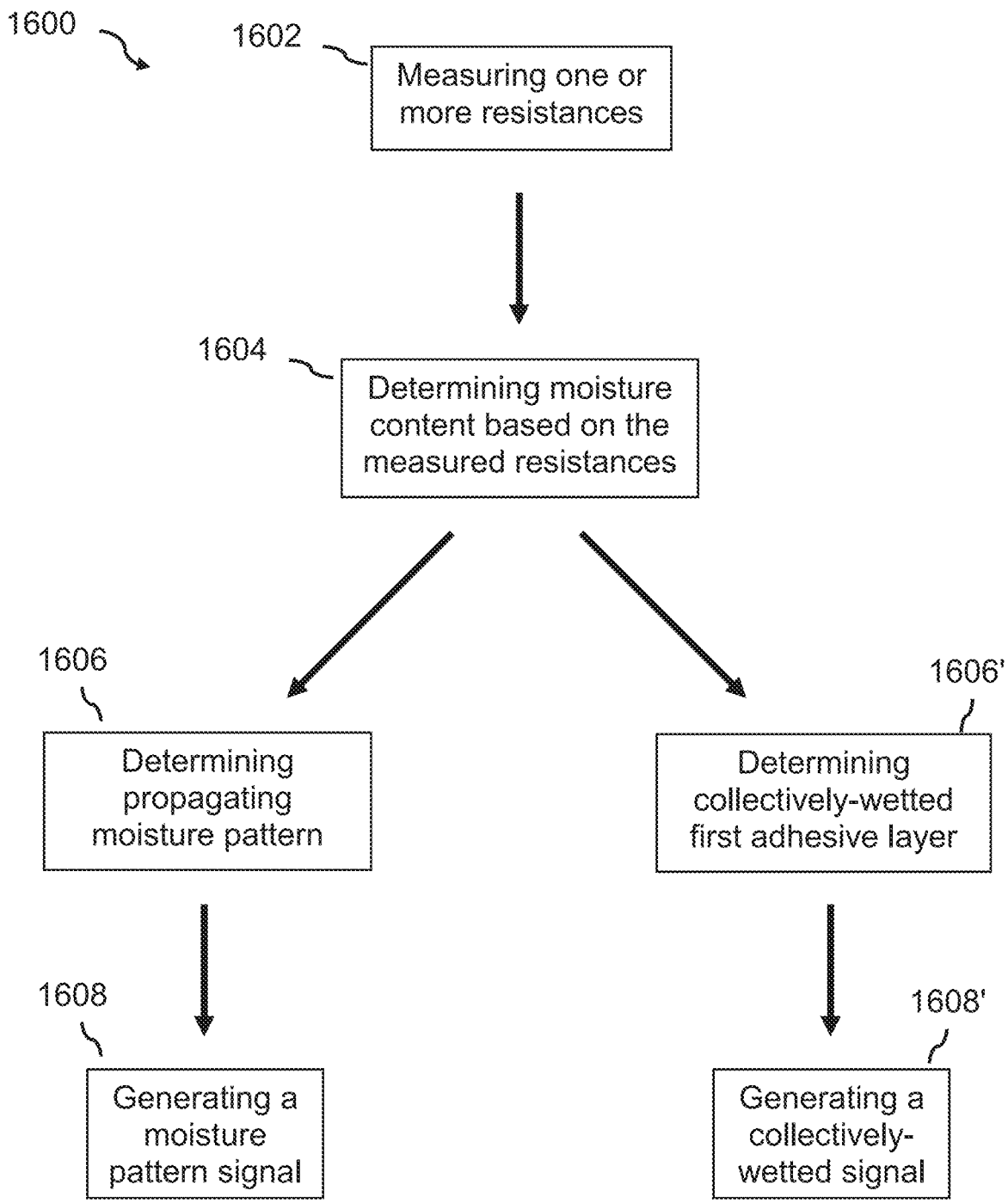
FIG. 18 depicts an illustrative method for detecting moisture content.

FIG. 18 depicts a flow-diagram illustrating a method 1600 of detecting moisture content in a base plate of an ostomy system. In embodiments, the base plate and the ostomy system may have the same or similar characteristics as the base plate, and/or the sensor assembly part, and the ostomy system described above in relation to FIGS. 1-17. In embodiments, the method 1600 comprises measuring 1602 one or more resistances at the one or more sensing zones using the plurality of electrodes. Each of the one or more resistances is measured by two of the plurality of electrodes at one of the one or more sensing zones.

The method 1600 may further comprise determining 1604 the moisture content in the first adhesive layer at each of the one or more sensing zones, by correlating the measured resistances to moisture contents. Determining 1604 may comprise converting the measured resistances to moisture contents by multiplying the measured resistances with a moisture-to-resistance ratio for each of the one or more sensing zones. The moisture-to-resistance ratio may be different in different sensing zones, reflecting the difference in electrode characteristics (e.g. length) in different sensing zones.

The method 1600 may further comprise determining 1606 the propagating moisture pattern. Determining 1606 the propagating moisture pattern may include detecting time-delays between resistance drops in at least two of the plurality of sensing zones, the resistance drops being below the trigger resistance values. In embodiments, determining 1606 the propagating moisture pattern may further comprise determining a propagating direction by connecting the sensing zones that have detected the propagating moisture pattern. Determining 1606 the propagating moisture pattern may further comprise determining a propagating velocity derived by dividing the distance traveled by the propagating moisture pattern (e.g. between sensing zones that have detected the propagating moisture pattern), by the time-delay between the detection of resistance drops at the sensing zones. Determining 1606 the propagating moisture pattern may further comprise determining a remaining usage time by considering the derived propagating velocity and the surface coverage of the first adhesive layer.

The method 1600 may further comprise generating 1608 a moisture pattern signal when the propagating moisture pattern is determined 1606. In embodiments, generating 1608 a moisture pattern signal may comprise deriving the propagating direction, the propagating velocity, and the remaining usage time.

The method 1600 may further comprise determining 1606' the collectively-wetted base plate. Determining 1606' the collectively-wetted base plate may include detecting substantially the same start time for resistance drops in the majority of one or more sensing zones 261.

The method 1600 may further comprise generating 1608' the collectively-wetted signal when the collectively-wetted base plate has been determined 1606'.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments of the present disclosure are set out in the following items:

1. An ostomy system configured to detect moisture content in a base plate and/or a sensor assembly part of the ostomy system, the ostomy system comprising:
    the base plate and/or the sensor assembly part including:
        a first adhesive layer having a distal surface and a proximal surface,
        a plurality of electrodes disposed on the distal surface of the first adhesive layer, and
        one or more sensing zones each covering one of one or more regions of the first adhesive layer, each of the one or more sensing zones including at least two of the plurality of electrodes; and
    a monitor device electrically coupled to the plurality of electrodes of the base plate and/or sensor assembly part, the monitor device being configured to (i) measure one or more resistances in the one or more sensing zones between the plurality of electrodes, each of the one or more resistances measured by two of the plurality of electrodes at one of the one or more sensing zones, and (ii) determine moisture content of the first adhesive layer at each of the one or more sensing zones based on the measured one or more resistances.

2. The ostomy system of item 1, wherein the one or more sensing zones are arranged at least one of circularly about, radially from, and concentrically about a central opening of the base plate and/or the sensor assembly part.

3. The ostomy system of any of the preceding items, wherein the monitor device is configured to detect a moisture pattern in the first adhesive layer based on the measured one or more resistances.

4. The ostomy system of any of the preceding items, wherein at least portions of the plurality of electrodes are distributed on concentric circles about the central opening of the base plate and/or the sensor assembly part and extend at least three-quarters of the circumferences of the corresponding concentric circles.

5. The ostomy system of any of the preceding items, wherein at least portions of the plurality of electrodes are distributed on concentric circles about the central opening of the base plate and/or the sensor assembly part and extend less than full circles to form open loops.

6. The ostomy system of any of the preceding items, wherein the monitor device is configured to generate a wetted signal when the moisture content in the first adhesive layer at any of the one or more sensing zones is determined to be elevated.

7. The ostomy system of any of the preceding items, wherein the monitor device is configured to generate a collectively-wetted signal when the moisture content in the first adhesive layer in a plurality of the one or more sensing zones are substantially the same and determined to be elevated.

8. The ostomy system of any of the preceding items, wherein the monitor device is configured to generate a propagating moisture signal when any of the measured one or more resistances measured at one of the one or more sensing zones drops below a first trigger resistance value, and another of the measured one or more resistances measured at another of the one or more sensing zones, delayed by a time-value exceeding a threshold time-value, drops below a second trigger resistance value.

9. The ostomy system of item 8, wherein the propagating moisture signal is indicative of a wetted region, the wetted region including sensing zones where the measured resistances have dropped below trigger resistance values.

10. The ostomy system of item 9, wherein the wetted region further include the regions between the sensing zones where the measured resistances have dropped below trigger resistance values.

11. The ostomy system of any of items 8-10, wherein the propagating moisture signal is indicative of a moisture propagating direction, the moisture propagating direction including a direction from one of the one or more sensing zones where the measured resistance first dropped below trigger resistance value, to another of the one or more sensing zones where the measured resistance next dropped below trigger resistance value.

12. The ostomy system of any of items 8-11, wherein the propagating moisture signal is indicative of a moisture propagating velocity, the moisture propagating velocity derived by dividing the distance between two of the one or more sensing zones that sequentially measured resistances dropping below trigger resistance values, by a time-delay between the measuring of the two resistance drops.

13. The ostomy system of any of the preceding items, wherein the first adhesive layer has an electrical conductivity and an adhesive strength that increases and decreases, respectively, with increasing moisture content in the first adhesive layer.

14. The ostomy system of any of the preceding items, wherein the plurality of electrodes comprises at least one of metallic, ceramic, polymeric, and carbonaceous materials.

15. The ostomy system of any of the preceding items, wherein the plurality of electrodes comprises one of silver and carbon.

16. The ostomy system of any of the preceding items, wherein the base plate and/or the sensor assembly part is at least one of bendable, flexible, twistable, and stretchable.

17. The ostomy system of any of the preceding items, further comprising a second adhesive layer coupled to the distal surface of the first adhesive layer.

18. The ostomy system of item 17, wherein the second adhesive layer is at least one of more adhesive, more moisture permeable, less moisture-absorbent, and lower in moisture capacity than the first adhesive layer.

19. The ostomy system of any of the preceding items, wherein the base plate and/or the sensor assembly part further comprises a first intermediate element between the first adhesive layer and a plurality of connection parts of the plurality of electrodes.

20. The ostomy system of item 19, wherein the first intermediate element is less electrically conductive than the first adhesive layer.

21. A method of detecting moisture content in a base plate and/or a sensor assembly part of an ostomy system, the ostomy system comprising the base plate and/or the sensor assembly part and a monitor device, the base plate and/or the sensor assembly part including a first adhesive layer having a distal surface and a proximal surface, a plurality of electrodes disposed on the distal surface of the first adhesive layer, and one or more sensing zones each covering one of one or more regions of the first adhesive layer, each of the one or more sensing zones including at least two of the plurality of electrodes, and the monitor device being electrically coupled to the plurality of electrodes of the base plate and/or the sensor assembly part, the method comprising:
    measuring one or more resistances in the one or more sensing zones via the plurality of electrodes, each of the one or more resistances measured between two of the plurality of electrodes at one of the one or more sensing zones; and
    determining moisture content of the first adhesive layer at each of the one or more sensing zones based on the measured one or more resistances.

22. A base plate and/or a sensor assembly part of an ostomy system, the base plate comprising:
    a first adhesive layer having a distal surface and a proximal surface,
    a plurality of electrodes disposed on the distal surface of the first adhesive layer, and
    one or more sensing zones each covering one of one or more regions of the first adhesive layer, each of the one or more sensing zones including at least two of the plurality of electrodes; and
wherein the plurality of electrodes are configured for measurements of one or more resistances in the one or more sensing zones between the plurality of electrodes, such as to determine moisture content of the first adhesive layer at each of the one or more sensing zones based on the measured one or more resistances.

23. A sensor assembly part of an ostomy system, the sensor assembly part comprising:
    a first adhesive layer having a distal surface and a proximal surface, the proximal surface being configured for attachment of the sensor assembly part to the skin surface of a user, the first adhesive layer having a stomal opening with a center point;
    a plurality of electrodes disposed on the distal surface of the first adhesive layer; and
    one or more sensing zones each covering one of one or more regions of the first adhesive layer, each of the one or more sensing zones including at least two of the plurality of electrodes,
wherein the plurality of electrodes is configured for measurements of one or more resistances in the one or more sensing zones between the plurality of electrodes, such as to determine moisture content of the first adhesive layer at each of the one or more sensing zones based on the measured one or more resistances.

24. The sensor assembly part of item 23, wherein the one or more sensing zones are arranged circularly about and/or radially from the center point of the stomal opening.

25. The sensor assembly part of any of items 23-24, wherein the one or more sensing zones includes a first sensing zone and a second sensing zone 26. The sensor assembly part of item 25, wherein the first sensing zone is arranged in a first angle space from the center point of the stomal opening and the second sensing zone is arranged in a second angle space from the center point.

27. The sensor assembly part of any of items 25-26, wherein the first sensing zone is arranged in a first radial space from the center point of the stomal opening and the second sensing zone is arranged in a second radial space from the center point.

28. The sensor assembly part of any of items 25-27, wherein the first sensing zone includes a first electrode and a ground electrode of the plurality of electrodes, and the second sensing zone includes a second electrode and the ground electrode of the plurality of electrodes.

29. The sensor assembly part of any of items 23-28, wherein at least portions of the plurality of electrodes extends about the stomal opening and extend at least three-quarters of the circumferences about the stomal opening.

30. The sensor assembly part of any of items 23-29, wherein at least portions of the plurality of electrodes extends about the stomal opening and extend less than full circles to form open loops.

31. The sensor assembly part of any of items 23-30, wherein the plurality of electrodes comprises at least one of metallic, ceramic, polymeric, and carbonaceous materials.

32. The sensor assembly part of any of items 23-31, wherein the plurality of electrodes comprises one of silver and carbon.

33. The sensor assembly part of any of items 23-32, wherein the base plate is at least one of bendable, flexible, twistable, and stretchable.

34. The sensor assembly part of any of items 23-33, further comprising a second adhesive layer coupled to the distal surface of the first adhesive layer.

35. The sensor assembly part of item 34 wherein the second adhesive layer is at least one of more adhesive, more moisture permeable, less moisture-absorbent, and lower in moisture capacity than the first adhesive layer.

36. The sensor assembly part of any of items 23-35, wherein the base plate further comprises a first intermediate element between the first adhesive layer and a plurality of connection parts of the plurality of electrodes.

37. The sensor assembly part of item 36, wherein the first intermediate element is less electrically conductive than the first adhesive layer.

LIST OF REFERENCES 1 ostomy system
2 ostomy appliance
4 base plate
4' base plate
4" base plate
6 monitor device
8 accessory device
10 server device
12 network
14 coupling member
16 coupling ring
18 stoma-receiving opening
18' stoma-receiving opening
18" stoma-receiving opening
18a stomal opening of first adhesive layer
18b stomal opening of second adhesive layer
18c stomal opening of electrode assembly
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200' first adhesive layer
200" first adhesive layer
200A distal surface of first adhesive layer
200B proximal surface of first adhesive layer
200B' proximal surface of first adhesive layer
200B" proximal surface of first adhesive layer
202 second adhesive layer
202' second adhesive layer
202" second adhesive layer
202A distal surface of second adhesive layer
202B proximal surface of second adhesive layer
202B' proximal surface of second adhesive layer
202B" proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
215 monitor interface
216 electrodes of electrode assembly
218 masking element
218A distal surface of masking element
218B proximal surface of masking element
220 electrode configuration
221 connection parts of the electrodes
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part 232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
261 one or more of sensing zones
261a first sensing zone
261b second sensing zone
261c third sensing zone
261' one or more of sensing zones
261a' first sensing zone
261b' second sensing zone
261c' third sensing zone
261" one or more of sensing zones
261a" first sensing zone
261b" second sensing zone
261c" third sensing zone
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
400 central region of the ostomy base plate
400' central region of the ostomy base plate
400" central region of the ostomy base plate
404 outer region of the ostomy base plate
404' outer region of the ostomy base plate
404" outer region of the ostomy base plate
700 sensor assembly part
$R_1$ resistance measured at first sensing zone
$R_1'$ resistance measured at first sensing zone
$R_2$ resistance measured at second sensing zone
$R_2'$ resistance measured at second sensing zone
$R_{i1}$ first primary resistance value
$R_{i1}'$ first primary resistance value
$R_{i2}$ second primary resistance value
$R_{i2}'$ second primary resistance value
$R_{f1}$ first secondary resistance value
$R_{f1}'$ first secondary resistance value
$R_{f2}$ second secondary resistance value
$R_{f2}'$ second secondary resistance value
$R_{t1}$ first trigger resistance value
$R_{t2}$ second trigger resistance value
$t_{w1}$ time when moisture content in the first sensing zone starts to increase
$t_{w1}'$ time when moisture content in the first sensing zone starts to increase
$t_{w2}$ time when moisture content in the second sensing zone starts to increase
$t_{w2}'$ time when moisture content in the second sensing zone starts to increase
$t_{t1}$ time when resistance measured in the first sensing zone drops below $R_{t1}$
$t_{t2}$ time when resistance measured in the second sensing zone drops below $R_{t2}$
$\Delta t$ time-delay
$R_{c1}$ first threshold resistance value
$R_{c2}$ second threshold resistance value
$t_{c1}$ time when resistance measured in the first sensing zone drops below $R_{c1}$
$t_{c2}$ time when resistance measured in the second sensing zone drops below $R_c$ The following is claimed:

1. An ostomy system configured to detect moisture content in a base plate of the ostomy system, the ostomy system comprising:
the base plate including:
a first adhesive layer having a distal surface and a proximal surface, the proximal surface being configured for attachment of the base plate to the skin surface of a user, the first adhesive layer having a stomal opening with a center point;
a plurality of electrodes disposed on the distal surface of the first adhesive layer; and
a plurality of sensing zones, each sensing zone covering one of a plurality of regions of the first adhesive layer and each sensing zone including at least two of the plurality of electrodes that comprise a pair of electrodes configured to measure a resistance of the first adhesive layer between the pair of electrodes, and
a monitor device electrically coupled to the plurality of electrodes of the base plate, the monitor device being configured to (i) measure one or more resistances of the first adhesive layer in each of the plurality of sensing zones, each of the one or more resistances of the first adhesive layer measured between the pair of electrodes in each sensing zone, and (ii) determine moisture content of the first adhesive layer in each of the plurality of sensing zones based on the measured one or more resistances of the first adhesive layer.

2. The ostomy system of claim 1, wherein the plurality of sensing zones are arranged circularly about and/or radially from the center point of the stomal opening.

3. The ostomy system of claim 1, wherein the plurality of sensing zones includes a first sensing zone and a second sensing zone.

4. The ostomy system of claim 3, wherein the first sensing zone is arranged in a first angle space from the center point of the stomal opening and the second sensing zone is arranged in a second angle space from the center point.

5. The ostomy system of claim 3, wherein the first sensing zone is arranged in a first radial space from the center point of the stomal opening and the second sensing zone is arranged in a second radial space from the center point.

6. The ostomy system of claim 3, wherein the first sensing zone includes a first electrode and a ground electrode of the plurality of electrodes, and the second sensing zone includes a second electrode and the ground electrode of the plurality of electrodes.

7. The ostomy system of claim 6, wherein the monitor device is configured to measure a first resistance of the adhesive layer in the first sensing zone between the first electrode and the ground electrode, and determine moisture content of the first adhesive layer in the first sensing zone based on the measured first resistance, and wherein the monitor device is configured to measure a second resistance of the adhesive layer in the second sensing zone between the second electrode and the ground electrode, and determine moisture content of the first adhesive layer in the second sensing zone based on the measured second resistance.

8. The ostomy system of claim 1, wherein the monitor device is configured to detect a moisture pattern in the first adhesive layer based on the measured one or more resistances.

9. The ostomy system of claim 1, wherein at least portions of the plurality of electrodes extends about the stomal opening and extend at least three-quarters of a circumference about the stomal opening.

10. The ostomy system of claim 1, wherein at least portions of the plurality of electrodes extends about the stomal opening and extend less than full circles to form open loops.

11. The ostomy system of claim 1, wherein the monitor device is configured to generate a wetted signal when the moisture content in the first adhesive layer in any of the plurality of sensing zones is determined to be elevated.

12. The ostomy system of claim 1, wherein the monitor device is configured to generate a collectively-wetted signal when the moisture content in the first adhesive layer in a plurality of the plurality of sensing zones are substantially the same and determined to be elevated.

13. The ostomy system of claim 1, wherein the monitor device is configured to determine a rate of change of each of the one or more resistances measured in the plurality of sensing zones.

14. The ostomy system of claim 13, wherein the monitor device is configured to determine a wetted type based on the determined rate of change.

15. The ostomy system of claim 14, wherein the wetted type is indicative of output when the determined rate of change is above a first rate threshold.

16. The ostomy system of claim 14, wherein the wetted type is indicative of sweat when the determined rate of change is below a second rate threshold.

17. The ostomy system of claim 1, wherein the monitor device is configured to generate a propagating moisture signal when a first resistance measured in a first sensing zone of the plurality of sensing zones drops below a first trigger resistance value, and a second resistance measured in a second sensing zone of the plurality of sensing zones, delayed by a time-value exceeding a threshold time-value, drops below a second trigger resistance value.

18. The ostomy system of claim 17, wherein the propagating moisture signal is indicative of a wetted region, the wetted region including sensing zones where the measured resistances have dropped below the first and second trigger resistance values.

19. The ostomy system of claim 18, wherein the wetted region further includes the regions between the sensing zones where the measured resistances have dropped below the first and second trigger resistance values.

20. The ostomy system of claim 17, wherein the propagating moisture signal is indicative of a moisture propagating direction, the moisture propagating direction including a direction from the first sensing zone to the second sensing zone.

21. The ostomy system of claim 17, wherein the propagating moisture signal is indicative of a moisture propagating velocity, the moisture propagating velocity derived by dividing the distance between the first sensing zone and the second sensing zone by a time-delay between the measuring of the two resistance drops.

22. The ostomy system of claim 1, wherein the first adhesive layer has an electrical conductivity that increases and an adhesive strength that decreases, with increasing moisture content in the first adhesive layer.

23. The ostomy system of claim 1, wherein the plurality of electrodes comprises at least one of metallic, ceramic, polymeric, and carbonaceous materials.

24. The ostomy system of claim 1, wherein the plurality of electrodes comprises one of silver and carbon.

25. The ostomy system of claim 1, wherein the base plate is at least one of bendable, flexible, twistable, and stretchable.

26. The ostomy system of claim 1, further comprising a second adhesive layer coupled to the distal surface of the first adhesive layer.

27. The ostomy system of claim 26, wherein the second adhesive layer is at least one of more adhesive, more moisture permeable, less moisture-absorbent, and lower in moisture capacity than the first adhesive layer.

28. The ostomy system of claim 1, wherein the base plate further comprises a first intermediate element between the first adhesive layer and a plurality of connection parts of the plurality of electrodes.

29. The ostomy system of claim 28, wherein the first intermediate element is less electrically conductive than the first adhesive layer.

30. A method of detecting moisture content in a base plate of an ostomy system, the ostomy system comprising the base plate and a monitor device, the base plate including a first adhesive layer having a distal surface and a proximal surface and a stomal opening with a center point, the proximal surface being configured for attachment of the base plate to the skin surface of a user; a plurality of electrodes disposed on the distal surface of the first adhesive layer; and a plurality of sensing zones, each sensing zone covering one of a plurality of regions of the first adhesive layer and each sensing zone including a pair of the plurality of electrodes, and the monitor device being electrically coupled to the plurality of electrodes of the base plate, the method comprising:

measuring one or more resistances of the first adhesive layer in each of the plurality of sensing zones, each of the one or more resistances of the first adhesive layer measured between the pair of electrodes in each sensing zone; and determining moisture content of the first adhesive layer in each of the plurality of sensing zones based on the measured one or more resistances of the first adhesive layer.

31. A base plate of an ostomy system, the base plate comprising:

a first adhesive layer having a distal surface and a proximal surface, the proximal surface being configured for attachment of the base plate to the skin surface of a user, the first adhesive layer having a stomal opening with a center point;

a plurality of electrodes disposed on the distal surface of the first adhesive layer; and a plurality of sensing zones, wherein each sensing zone of the plurality of sensing zones:
  covers a region of the first adhesive layer; and
  includes a pair of electrodes of the plurality of electrodes configured to measure a resistance of the first adhesive layer between the pair of electrodes in the sensing zone to determine moisture content of the first adhesive layer based on the measured resistance of the adhesive layer between the pair of electrodes.

* * * * *